(12) United States Patent
Zhao et al.

(10) Patent No.: US 12,624,368 B2
(45) Date of Patent: May 12, 2026

(54) NUCLEIC ACID MOLECULES AND DUAL-FUNCTIONAL PEPTIDES HAVING ANTIVIRAL ACTIVITY AND DELIVERY ACTIVITY, COMPOSITIONS AND METHODS THEREOF

(71) Applicant: THE UNIVERSITY OF HONG KONG, Hong Kong (HK)

(72) Inventors: Hanjun Zhao, Shanghai (CN); Kai Wang Kelvin To, Pokfulam (HK); Kwok Yung Yuen, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 1180 days.

(21) Appl. No.: 17/049,974

(22) PCT Filed: Apr. 26, 2019

(86) PCT No.: PCT/CN2019/084612
§ 371 (c)(1),
(2) Date: Oct. 23, 2020

(87) PCT Pub. No.: WO2019/206285
PCT Pub. Date: Oct. 31, 2019

(65) Prior Publication Data
US 2021/0238629 A1     Aug. 5, 2021

Related U.S. Application Data

(60) Provisional application No. 62/668,872, filed on May 9, 2018, provisional application No. 62/663,076, filed on Apr. 26, 2018.

(51) Int. Cl.
| | |
|---|---|
| *C12N 15/62* | (2006.01) |
| *A61K 9/00* | (2006.01) |
| *A61K 39/145* | (2006.01) |
| *A61P 31/16* | (2006.01) |
| *C07K 14/005* | (2006.01) |
| *C12N 15/86* | (2006.01) |
| *A61K 39/00* | (2006.01) |

(52) U.S. Cl.
CPC ............. *C12N 15/86* (2013.01); *A61K 9/007* (2013.01); *A61K 9/0073* (2013.01); *A61K 39/145* (2013.01); *A61P 31/16* (2018.01);

*C07K 14/005* (2013.01); *C12N 15/62* (2013.01); *A61K 2039/5256* (2013.01); *A61K 2039/54* (2013.01); *A61K 2039/545* (2013.01); *A61K 2039/572* (2013.01); *C12N 2740/16022* (2013.01); *C12N 2740/16032* (2013.01); *C12N 2740/16043* (2013.01); *C12N 2760/16122* (2013.01); *C12N 2760/16134* (2013.01); *C12N 2760/16143* (2013.01)

(58) Field of Classification Search
None
See application file for complete search history.

(56) References Cited

U.S. PATENT DOCUMENTS

| | | | | |
|---|---|---|---|---|
| 5,789,245 A * | 8/1998 | Dubensky, Jr. | ...... | C07K 14/755 435/325 |
| 8,691,215 B2 | 4/2014 | Dimmock | | |
| 10,125,374 B2 * | 11/2018 | Muster | ................. | A61K 39/395 |
| 2009/0042782 A1 * | 2/2009 | Coignet | ................. | A61P 35/00 435/6.16 |
| 2023/0158136 A1 * | 5/2023 | Zhao | ..................... | C12N 15/85 424/209.1 |

OTHER PUBLICATIONS

International Search Report and Written Opinion for International Application No. PCT/CN2019/084612 mailed on Aug. 1, 2019, 11 pages.

* cited by examiner

*Primary Examiner* — Anoop K Singh
*Assistant Examiner* — Constantina E Stavrou
(74) *Attorney, Agent, or Firm* — Amin, Turocy & Watson, LLP

(57) ABSTRACT

Disclosed are delivery and expression systems of multiple antiviral therapeutic molecules. The therapeutic molecules include a novel class of dual-functional peptide and defective interfering genes of a virus. Also disclosed are compositions comprising the therapeutic molecules that are useful for the treatment and prevention of viral infections. Also disclosed herein are the method of making and using a vector that expresses the therapeutic molecules. Therapeutic molecules include cellular components such as RNA, DNA, peptide, proteins or combination thereof.

Figure 1:
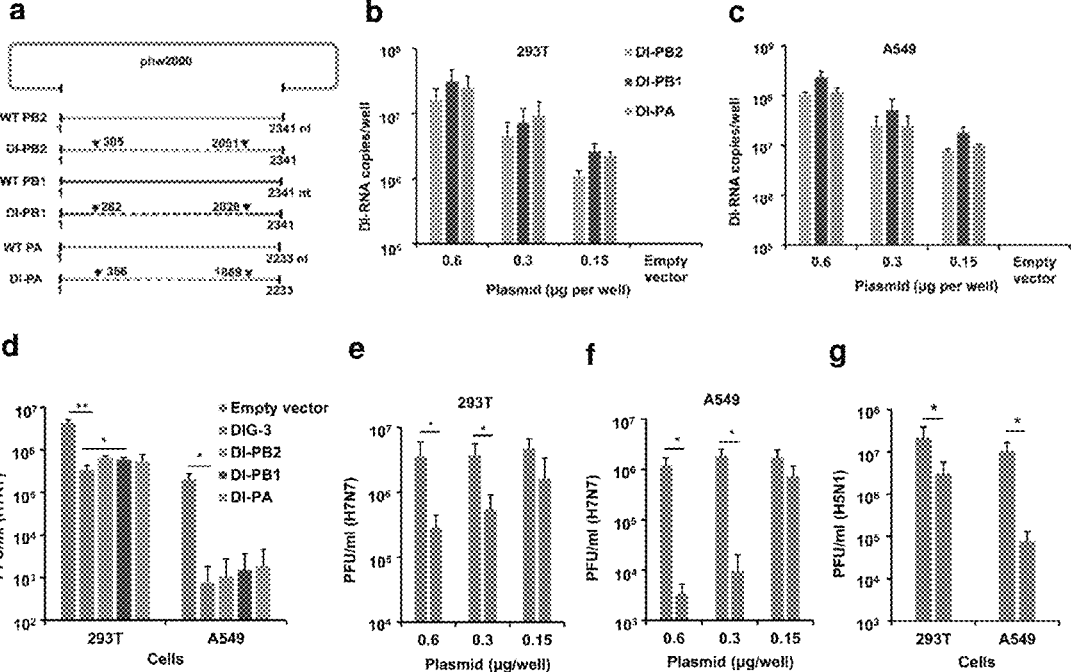

10 Claims, 8 Drawing Sheets
Specification includes a Sequence Listing.

SEQUENCE LISTING

```
<160> NUMBER OF SEQ ID NOS: 40

<210> SEQ ID NO 1
<211> LENGTH: 37
<212> TYPE: PRT
<213> ORGANISM: Artificial Sequence
<220> FEATURE:
<223> OTHER INFORMATION: synthetic peptide

<400> SEQUENCE: 1

Tyr Gly Arg Lys Lys Arg Arg Gln Arg Arg Arg Cys Trp Gly Pro Cys
1               5                   10                  15

Pro Thr Ala Phe Arg Gln Ile Gly Asn Cys Gly Arg Phe Arg Val Arg
            20                  25                  30

Cys Cys Arg Ile Arg
            35

<210> SEQ ID NO 2
<211> LENGTH: 36
<212> TYPE: PRT
<213> ORGANISM: Artificial Sequence
<220> FEATURE:
<223> OTHER INFORMATION: synthetic sequence

<400> SEQUENCE: 2

Tyr Gly Arg Lys Lys Arg Arg Gln Arg Arg Arg Cys Trp Arg Pro Cys
1               5                   10                  15

Pro Arg Ala Phe Arg Lys Arg Asn Cys Gly Arg Phe Arg Ile Arg Cys
            20                  25                  30

Cys Arg Ile Arg
        35

<210> SEQ ID NO 3
<211> LENGTH: 33
<212> TYPE: PRT
```

<213> ORGANISM: Artificial Sequence
<220> FEATURE:
<223> OTHER INFORMATION: synthetic peptide

<400> SEQUENCE: 3

Tyr Gly Arg Lys Lys Arg Arg Gln Arg Arg Cys Trp Arg Pro Cys
1               5                   10                  15

Pro Ser Phe Arg Gln Leu Cys Gly Arg Phe Arg Ile Arg Cys Arg Ile
            20                  25                  30

Arg

<210> SEQ ID NO 4
<211> LENGTH: 26
<212> TYPE: PRT
<213> ORGANISM: Artificial Sequence
<220> FEATURE:
<223> OTHER INFORMATION: synthetic peptide

<400> SEQUENCE: 4

Cys Trp Gly Pro Cys Pro Thr Ala Phe Arg Gln Ile Gly Asn Cys Gly
1               5                   10                  15

Arg Phe Arg Val Arg Cys Cys Arg Ile Arg
            20                  25

<210> SEQ ID NO 5
<211> LENGTH: 25
<212> TYPE: PRT
<213> ORGANISM: Artificial Sequence
<220> FEATURE:
<223> OTHER INFORMATION: synthetic peptide

<400> SEQUENCE: 5

Cys Trp Arg Pro Cys Pro Arg Ala Phe Arg Lys Arg Asn Cys Gly Arg
1               5                   10                  15

Phe Arg Ile Arg Cys Cys Arg Ile Arg
            20                  25

<210> SEQ ID NO 6
<211> LENGTH: 22
<212> TYPE: PRT
<213> ORGANISM: Artificial Sequence
<220> FEATURE:
<223> OTHER INFORMATION: synthetic peptide

<400> SEQUENCE: 6

Cys Trp Arg Pro Cys Pro Ser Phe Arg Gln Leu Cys Gly Arg Phe Arg
1               5                   10                  15

Ile Arg Cys Arg Ile Arg
            20

<210> SEQ ID NO 7
<211> LENGTH: 11
<212> TYPE: PRT
<213> ORGANISM: Artificial Sequence
<220> FEATURE:
<223> OTHER INFORMATION: synthetic peptide

<400> SEQUENCE: 7

Tyr Gly Arg Lys Lys Arg Arg Gln Arg Arg Arg
1               5                   10

<210> SEQ ID NO 8
<211> LENGTH: 30
<212> TYPE: PRT

-continued

```
<213> ORGANISM: Artificial Sequence
<220> FEATURE:
<223> OTHER INFORMATION: synthetic peptide

<400> SEQUENCE: 8

Asn Gly Ala Ile Cys Trp Gly Pro Cys Pro Thr Ala Phe Arg Gln Ile
1               5                   10                  15

Gly Asn Cys Gly His Phe Lys Val Arg Cys Cys Lys Ile Arg
            20                  25                  30

<210> SEQ ID NO 9
<211> LENGTH: 33
<212> TYPE: PRT
<213> ORGANISM: Artificial Sequence
<220> FEATURE:
<223> OTHER INFORMATION: synthetic peptide

<400> SEQUENCE: 9

Asn Gly Ala Ile Cys Trp Gly Pro Cys Pro Thr Ala Phe Arg Gln Ile
1               5                   10                  15

Gly Asn Cys Gly His Phe Lys Val Arg Cys Cys Lys Ile Arg Asp Glu
            20                  25                  30

Asp

<210> SEQ ID NO 10
<211> LENGTH: 28
<212> TYPE: DNA
<213> ORGANISM: Artificial Sequence
<220> FEATURE:
<223> OTHER INFORMATION: synthetic sequence

<400> SEQUENCE: 10
tattggtctc agggagcgaa agcaggtc                                       28

<210> SEQ ID NO 11
<211> LENGTH: 22
<212> TYPE: DNA
<213> ORGANISM: Artificial Sequence
<220> FEATURE:
<223> OTHER INFORMATION: synthetic sequence

<400> SEQUENCE: 11
ggtgatacca tcactcggtc tg                                             22

<210> SEQ ID NO 12
<211> LENGTH: 53
<212> TYPE: DNA
<213> ORGANISM: Artificial Sequence
<220> FEATURE:
<223> OTHER INFORMATION: synthetic sequence

<400> SEQUENCE: 12
cgccggatca gaccgagtga tggtatcacc taactgaaga cccagatgaa ggc          53

<210> SEQ ID NO 13
<211> LENGTH: 34
<212> TYPE: DNA
<213> ORGANISM: Artificial Sequence
<220> FEATURE:
<223> OTHER INFORMATION: synthetic sequence

<400> SEQUENCE: 13
atatggtctc gtattagtag aaacaaggtc gttt                                34
```

-continued

```
<210> SEQ ID NO 14
<211> LENGTH: 28
<212> TYPE: DNA
<213> ORGANISM: Artificial Sequence
<220> FEATURE:
<223> OTHER INFORMATION: synthetic sequence

<400> SEQUENCE: 14
tattcgtctc agggagcaaa agcaggca                                        28

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence

<400> SEQUENCE: 15
atctgtttgg gcataaccac                                                 20

<210> SEQ ID NO 16
<211> LENGTH: 55
<212> TYPE: DNA
<213> ORGANISM: Artificial Sequence
<220> FEATURE:
<223> OTHER INFORMATION: Synthetic sequence

<400> SEQUENCE: 16
acaatgaacc aagtggttat gcccaaacag atcaaaagaa atcgatccat cttga          55

<210> SEQ ID NO 17
<211> LENGTH: 33
<212> TYPE: DNA
<213> ORGANISM: Artificial Sequence
<220> FEATURE:
<223> OTHER INFORMATION: Synthetic sequence

<400> SEQUENCE: 17
atatcgtctc gtattagtag aaacaaggca ttt                                  33

<210> SEQ ID NO 18
<211> LENGTH: 29
<212> TYPE: DNA
<213> ORGANISM: Artificial Sequence
<220> FEATURE:
<223> OTHER INFORMATION: Synthetic sequence

<400> SEQUENCE: 18
tattcgtctc agggagcaaa agcaggtac                                       29

<210> SEQ ID NO 19
<211> LENGTH: 25
<212> TYPE: DNA
<213> ORGANISM: Artificial Sequence
<220> FEATURE:
<223> OTHER INFORMATION: Synthetic sequence

<400> SEQUENCE: 19
tcatacaaat ctggtagaaa ctttg                                           25

<210> SEQ ID NO 20
<211> LENGTH: 53
<212> TYPE: DNA
<213> ORGANISM: Artificial Sequence
<220> FEATURE:
<223> OTHER INFORMATION: Synthetic sequence
```

-continued

```
<400> SEQUENCE: 20
agaaaccaaa gtttctacca gatttgtatg agagagtccc ccaaaggagt gga          53

<210> SEQ ID NO 21
<211> LENGTH: 33
<212> TYPE: DNA
<213> ORGANISM: Artificial Sequence
<220> FEATURE:
<223> OTHER INFORMATION: Synthetic sequence

<400> SEQUENCE: 21
atatcgtctc gtattagtag aaacaaggta ctt                                33

<210> SEQ ID NO 22
<211> LENGTH: 22
<212> TYPE: DNA
<213> ORGANISM: Artificial Sequence
<220> FEATURE:
<223> OTHER INFORMATION: Synthetic sequence

<400> SEQUENCE: 22
aactaatctg tatggattca tc                                            22

<210> SEQ ID NO 23
<211> LENGTH: 20
<212> TYPE: DNA
<213> ORGANISM: Artificial Sequence
<220> FEATURE:
<223> OTHER INFORMATION: Synthetic sequence

<400> SEQUENCE: 23
atctcgataa cgcagtactt                                               20

<210> SEQ ID NO 24
<211> LENGTH: 21
<212> TYPE: DNA
<213> ORGANISM: Artificial Sequence
<220> FEATURE:
<223> OTHER INFORMATION: Synthetic sequence

<400> SEQUENCE: 24
atggctcttc agctattcat c                                             21

<210> SEQ ID NO 25
<211> LENGTH: 21
<212> TYPE: DNA
<213> ORGANISM: Artificial Sequence
<220> FEATURE:
<223> OTHER INFORMATION: Synthetic sequence

<400> SEQUENCE: 25
atctgatacc aacagtcctg c                                             21

<210> SEQ ID NO 26
<211> LENGTH: 19
<212> TYPE: DNA
<213> ORGANISM: Artificial Sequence
<220> FEATURE:
<223> OTHER INFORMATION: Synthetic sequence

<400> SEQUENCE: 26
aaactgggaa actgtgaag                                                19

<210> SEQ ID NO 27
<211> LENGTH: 18
```

-continued

```
<212> TYPE: DNA
<213> ORGANISM: Artificial Sequence
<220> FEATURE:
<223> OTHER INFORMATION: Synthetic sequence

<400> SEQUENCE: 27
atctgctgga atagcgtc                                                                 18

<210> SEQ ID NO 28
<211> LENGTH: 23
<212> TYPE: DNA
<213> ORGANISM: Artificial Sequence
<220> FEATURE:
<223> OTHER INFORMATION: Synthetic sequence

<400> SEQUENCE: 28
tatttgcaac actacagggg ctg                                                           23

<210> SEQ ID NO 29
<211> LENGTH: 24
<212> TYPE: DNA
<213> ORGANISM: Artificial Sequence
<220> FEATURE:
<223> OTHER INFORMATION: Synthetic sequence

<400> SEQUENCE: 29
atgcatacaa gctgttgaat accg                                                          24

<210> SEQ ID NO 30
<211> LENGTH: 23
<212> TYPE: DNA
<213> ORGANISM: Artificial Sequence
<220> FEATURE:
<223> OTHER INFORMATION: Synthetic sequence

<400> SEQUENCE: 30
caccgaaact ggagcaccgc aac                                                           23

<210> SEQ ID NO 31
<211> LENGTH: 23
<212> TYPE: DNA
<213> ORGANISM: Artificial Sequence
<220> FEATURE:
<223> OTHER INFORMATION: Synthetic sequence

<400> SEQUENCE: 31
tttgttcatc ttcaagtatt cct                                                           23

<210> SEQ ID NO 32
<211> LENGTH: 19
<212> TYPE: DNA
<213> ORGANISM: Artificial Sequence
<220> FEATURE:
<223> OTHER INFORMATION: Synthetic sequence

<400> SEQUENCE: 32
gataacggaa atgattcct                                                                19

<210> SEQ ID NO 33
<211> LENGTH: 19
<212> TYPE: DNA
<213> ORGANISM: Artificial Sequence
<220> FEATURE:
<223> OTHER INFORMATION: Synthetic sequence

<400> SEQUENCE: 33
```

-continued

```
tcagaactgc ggactcaac                                                    19

<210> SEQ ID NO 34
<211> LENGTH: 20
<212> TYPE: DNA
<213> ORGANISM: Artificial Sequence
<220> FEATURE:
<223> OTHER INFORMATION: Synthetic sequence

<400> SEQUENCE: 34
caatgacccc ttcattgacc                                                   20

<210> SEQ ID NO 35
<211> LENGTH: 20
<212> TYPE: DNA
<213> ORGANISM: Artificial Sequence
<220> FEATURE:
<223> OTHER INFORMATION: Synthetic sequence

<400> SEQUENCE: 35
ttgattttgg agggatctcg                                                   20

<210> SEQ ID NO 36
<211> LENGTH: 24
<212> TYPE: DNA
<213> ORGANISM: Artificial Sequence
<220> FEATURE:
<223> OTHER INFORMATION: Synthetic sequence

<400> SEQUENCE: 36
tgtgatggtg ggaatgggtc agaa                                              24

<210> SEQ ID NO 37
<211> LENGTH: 24
<212> TYPE: DNA
<213> ORGANISM: Artificial Sequence
<220> FEATURE:
<223> OTHER INFORMATION: Synthetic sequence

<400> SEQUENCE: 37
tgtggtgcca gatcttctcc atgt                                              24

<210> SEQ ID NO 38
<211> LENGTH: 701
<212> TYPE: DNA
<213> ORGANISM: Artificial Sequence
<220> FEATURE:
<223> OTHER INFORMATION: Synthetic sequence

<400> SEQUENCE: 38
agcaaaagca ggtactgatt caaaatggaa gattttgtgc gacaatgctt caatccgatg       60
attgtcgagc ttgcggaaaa ggcaatgaaa gagtatggag aggacctgaa aatcgaaaca      120
aacaaatttg cagcaatatg cactcacttg gaagtgtgct tcatgtattc agattttcac      180
ttcatcgatg agcaaggcga gtcaatagtc gtagaacttg gcgatccaaa tgcacttttg      240
aagcacagat ttgaaataat cgagggaaga gatcgcacaa tagcctggac agtaataaac      300
agtatttgca acactacagg ggctgagaaa ccaaagtttc taccagattt gtatgagaga      360
gtcccccaaa ggagtggagg aaggttccat tgggaaggtc tgcagaactt tattggcaaa      420
gtcggtattc aacagcttgt atgcatctcc acaactggaa ggattttcag ctgaatcaag      480
aaaactgctt cttatcgttc aggctcttag ggacaacctg gaacctggga cctttgatct      540
tggggggcta tatgaagcaa ttgaggagtg cctgattaat gatccctggg ttttgcttaa      600
```

```
tgcttcttgg ttcaactcct tcctcacaca tgcattgaga tagttgtggc aatgctacta      660
tttgctatcc atactgtcca aaaaagtacc ttgtttctac t                          701

<210> SEQ ID NO 39
<211> LENGTH: 596
<212> TYPE: DNA
<213> ORGANISM: Artificial Sequence
<220> FEATURE:
<223> OTHER INFORMATION: Synthetic sequence

<400> SEQUENCE: 39
agcaaaagca ggcaaaccat ttgaatggat gtcaatccga ctttactttt cttaaaagtg       60
ccagcacaaa atgctataag cacaactttc ccttatactg gagaccctcc ttacagccat      120
gggacaggaa caggatacac catggatact gtcaacagga cacatcagta ctcagaaagg      180
ggaagatgga caacaaacac cgaaactgga gcaccgcaac tcaacccgat tgatgggcca      240
ctgccagaag acaatgaacc aagtggttat gcccaaacag atcaaaagaa atcgatccat      300
cttgaataca agccaaagag gaatacttga agatgaacaa atgtaccaaa agtgctgcaa      360
cttatttgaa aaattcttcc ccagcagttc atacagaaga ccagtcggga tatccagtat      420
ggtggaggct atggtttcca gagcccgaat tgatgcacga attgatttcg aatctggaag      480
gataaagaaa gaggagttca ctgagatcat gaagatctgt tccaccattg aagagctcag      540
acggcaaaaa tagtgaattt agcttgtcct tcatgaaaaa atgccttgtt tctact         596

<210> SEQ ID NO 40
<211> LENGTH: 596
<212> TYPE: DNA
<213> ORGANISM: Artificial Sequence
<220> FEATURE:
<223> OTHER INFORMATION: Synthetic sequence

<400> SEQUENCE: 40
agcgaaagca ggtcaattat attcaatatg gaaagaataa aagaactaag gaatctaatg       60
tcgcagtctc gcactcgcga gatactcaca aaaaccaccg tggaccatat ggccataatc      120
aagaagtaca catcaggaag acaggagaag aacccagcac ttaggatgaa atggatgatg      180
gcaatgaaat atccaattac agcagacaag aggataacgg aaatgattcc tgagagaaat      240
gagcagggac aaactttatg gagtaaaatg aatgacgccg gatcagaccg agtgatggta      300
tcacctaact gaagacccag atgaaggcac agctggagtt gagtccgcag ttctgagagg      360
attcctcatt ctgggcaaag aagacaggag atatggacca gcattaagca taaatgaact      420
gagcaacctt gcgaaaggag agaaggctaa tgtgctaatt gggcaaggag acgtggtgtt      480
ggtaatgaaa cggaaacgga actctagcat acttactgac agccagacag cgaccaaaag      540
aattcggatg gccatcaatt agtgtcgaat agtttaaaaa cgaccttgtt tctact         596
```

NUCLEIC ACID MOLECULES AND DUAL-FUNCTIONAL PEPTIDES HAVING ANTIVIRAL ACTIVITY AND DELIVERY ACTIVITY, COMPOSITIONS AND METHODS THEREOF

1. FIELD OF THE INVENTION

Disclosed are delivery and expression systems of multiple antiviral therapeutic molecules. The therapeutic molecules include a novel class of dual-functional peptide and defective interfering genes of a virus. Also disclosed are compositions comprising the therapeutic molecules that are useful for the treatment and prevention of viral infections. Also disclosed herein are the method of making and using a vector that expresses the therapeutic molecules.

2. BACKGROUND OF THE INVENTION

Seasonal influenza virus annually causes over 3 to 5 million cases of severe illness with about 0.25 million deaths globally. Antigenically-shifted zoonotic influenza viruses pose threats of another pandemic[1-3]. Neuraminidase inhibitors, such as oseltamivir and zanamivir, have been used clinically for many years. However, human isolates of A(H1N1)pdm09, A(H3N2), A(H5N1) and A(H7N9) resistant to neuraminidase inhibitors have been found[4-7]. Convalescent blood products with high titer of specific neutralizing antibody have been shown to improve survival, but are not readily available[8]. Thus, broad spectrum antivirals with low possibility to induce resistance are urgently needed for controlling influenza virus infections.

Defective interfering (DI) viruses, which are arisen naturally during viral replication with internal deletions in viral genes[9, 10], can compete with the growth of wild-type virus and therefore suppress the replication of wild-type virus by interfering with the expression of the cognate full-length RNAs[9, 11, 12]. Though influenza DI virus (DIV) has been shown to be effective in vivo as a potential broad-spectrum antiviral with low risk for inducing resistance[13-16], there are several concerns of influenza DIV used as therapeutic agents. Firstly, influenza DIV may reassort with wild-type influenza A virus to generate novel reassortants[17]. Secondly, neutralizing antibody may develop against the DIV and affect the antiviral effect in subsequent use. Delivering defective interfering genes (DIG) as an antiviral may avoid the risk of generating new reassortant virus and the problem of unwanted immunogenicity.

There is limited efficacy of current antivirals and antiviral-resistant mutations impair anti-influenza treatment. Thus, there is a strong need for high efficiency antiviral molecules to prevent and treat influenza. It is in regard to these issues and others that the present disclosure is provided.

3. SUMMARY

Provided herein are defective interfering viruses with internal deletions in viral genes that compete with the growth of wild-type, non-detective virus. Also provided are defective interfering viruses that suppress the replication of wild-type virus by interfering with the expression of cognate full-length RNAs.

Provided herein is a vector comprising one or more viral genes wherein each of the viral gene comprises a deletion to form a detective interfering gene (DIG), said vector expresses one or more nucleic acid molecules that interfere with expression of one or more wild-type viral genes that do not comprise the deletion.

Provided herein is a composition comprising the disclosed vector and a pharmaceutical carrier.

Provided herein is a composition comprising the one or more nucleic acid molecules expressed from the disclosed vector and a TAT-P1 peptide.

Also provided herein is a cell comprising the disclosed vector.

Provided herein is a fusion protein comprising HIV-1 Tat peptide (TAT) and a cationic peptide P1 (derived from P9). In one embodiment, provided herein is a fusion protein comprising TAT and P2. In one embodiment, provided herein is a fusion protein comprising TAT and P3.

Provided herein is a method of preventing or treating a subject against avian or seasonal influenza virus, said method comprises administering to the subject an effective amount of the vector disclosed herein.

In certain embodiments, viral replication of wild-type virus is significantly reduced when treated with defective interfering virus. In certain embodiments, the replication of viruses that are treated with DIG is 10-20%, 20-30%, 30-40%, 40-50%, 50-60%, 60-70%, 70-80%, 80-90%, 90-100% reduced as compared to wild-type viruses that are not treated with DIG. In certain embodiments, 293T cells or A549 cells are transfected with DIG.

Also disclosed is a kit, a medical device, or an inhaler, comprising the disclosed vector.

4. BRIEF DESCRIPTION OF THE DRAWINGS

The invention is illustrated in the figures of the accompanying drawings which are meant to be exemplary and not limiting, in which like references are intended to refer to like or corresponding parts, and in which:

FIG. 1 Construction and antiviral activity of defective interfering genes (DIG). (a) The plasmid construction of DI-PB2, DI-PB1 and DI-PA. The indicated sequences of shortened viral polymerase gene PB2, PB1 and PA were inserted into phw2000, respectively. Dotted lines indicate the internal deletion of wild-type (WT) viral polymerase genes. (b, c) DI RNA expression in 293T and A549 cells. The plasmids of DI-PB2, DI-PB1 and DI-PA were co-transfected into cells with the indicated concentrations. At 24 h post transfection, DI RNAs were extracted from cells and digested by DNase I for RT-qPCR. Empty vector was as a negative control for RT-qPCR. (d) Anti-A(H7N7) virus activity of individual plasmid of DI-PB2, DI-PB1 and DI-PA or three combined plasmid DIG (DIG-3, 0.6 µg per well). (e, f) Dose dependent anti-A(H7N7) virus activity of DIG-3 in 293T and A549 cells. (g) Anti-A(H5N1) virus activity of DIG-3. Empty vector phw2000 and plasmids with DIG were individually transfected to cells. At 24 h post transfection, cells were infected with A(H7N7) or A(H5N1) virus at MOI=0.005 and cell supernatants were collected at 40 h post infection. Viral titers in the supernatants were detected by plaque assay. Data were presented as mean±SD of three independent experiments. * indicates P<0.05. ** indicates P<0.01. P values were calculated by the two-tailed Student's t test.

Figure 2:
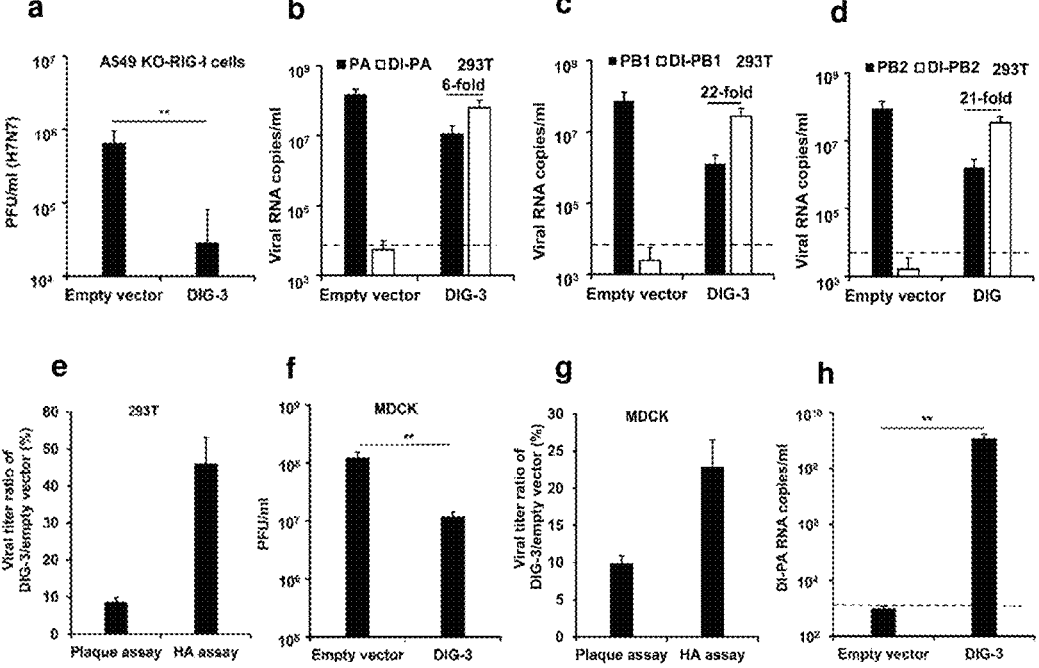

FIG. 2 DIG could be packaged to generate defective interfering virus and competitively inhibit normal viral replication. (a) Antiviral activity of DIG-3 in A549-Dual KO-RIG-I cells. The A549-Dual KO-RIG-I cells were infected with A(H7N7) virus at 24 h post transfection of empty vector or DIG-3 (0.6 µg per well). Viral titers in cell supernatants of 40 h post infection were measured by plaque assay. (b-d) Full-length PA, full-length PB1, full-length PB2, DI-PA, DI-PB1 and DI-PB2 RNA levels in the supernatants of A(H7N7)-infected cells transfected with empty vector or DIG-3 before viral infection. (e) The percentage of DIG-3-treated virus compared with empty vector-treated virus in supernatants of 293T cells. Viral titers were measured by plaque assay and HA assay. (f) The passaged viral titers in supernatants of MDCK cells which were infected by the supernatant virus of A(H7N7)-infected 293T cells transfected with empty vector or DIG-3. (g) The virus titer ratio of DIG-3-treated virus compared with empty vector-treated virus in supernatants of MDCK cells. Viral titers were measured by plaque assay and HA assay. (h) The DI-PA RNA levels of passaged virus in the supernatants of MDCK cells. Dotted lines mean the value of detection limitation of RT-qPCR. Data were presented as mean±SD of three independent experiments. * indicates P<0.05. ** indicates P<0.01.

Figure 3:
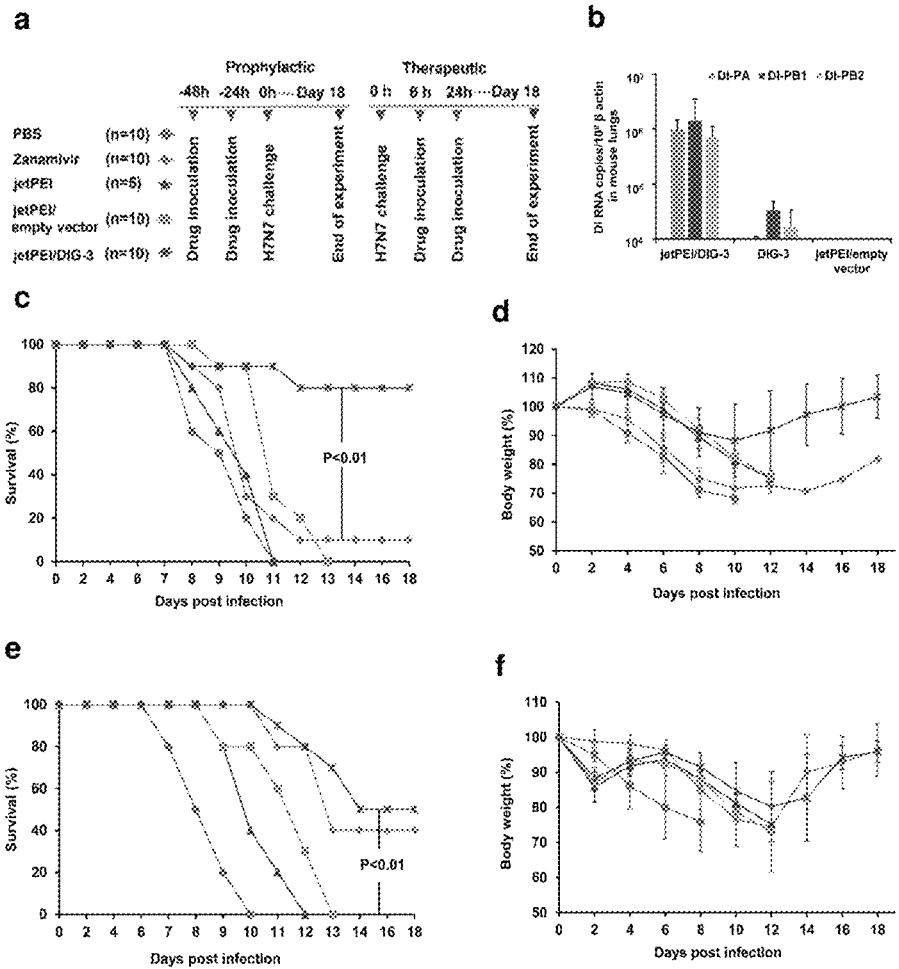

FIG. 3 The jetPEI/DIG-3 could provide potent anti-A (H7N7) virus efficacy in mice. (a) Experiment design for evaluating antiviral efficacy of jetPEI® transfection agent/ DIG-3 linear polyethylenimine derivative/DIG-3 in mice. (b) Expression of DI-PA, DI-PB1 and DI-PB2 RNAs in mouse lungs when jetPEI® transfection agent/DIG-3 (5 µg per mouse), DIG-3, jetPEI® transfection agent/empty vector were intratracheally inoculated to mouse lungs. Three mice in each group were included. (c, d) Prophylactic efficacy of jetPEI® transfection agent/DIG-3 against A(H7N7) virus. (e, f) Therapeutic efficacy of jetPEI/DIG-3 against A(H7N7) virus. For prophylactic experiment, 40 µl of PBS (n=10), zanamivir (50 µg in PBS, n=10), jetPEI® transfection agent (0.7 µl in 5% glucose solution, n=5), jetPEI/empty vector (0.7 µl/5.0 µg in 5% glucose solution, n=10), and jetPEI/ DIG-3 (0.7 µl/5.0 µg in 5% glucose solution, n=10) were intratracheally inoculated to corresponding mice at 48 h and 24 h before viral inoculation. For therapeutic experiment, PBS, zanamivir, jetPEI® transfection agent, jetPEI® transfection agent/empty vector and jetPEI® transfection agent/ DIG-3 were intratracheally inoculated to corresponding mice at 6 h and 24 h after viral inoculation. Survivals and body weight data were generated from 5-10 mice in each group with mean±SD.

Figure 4:
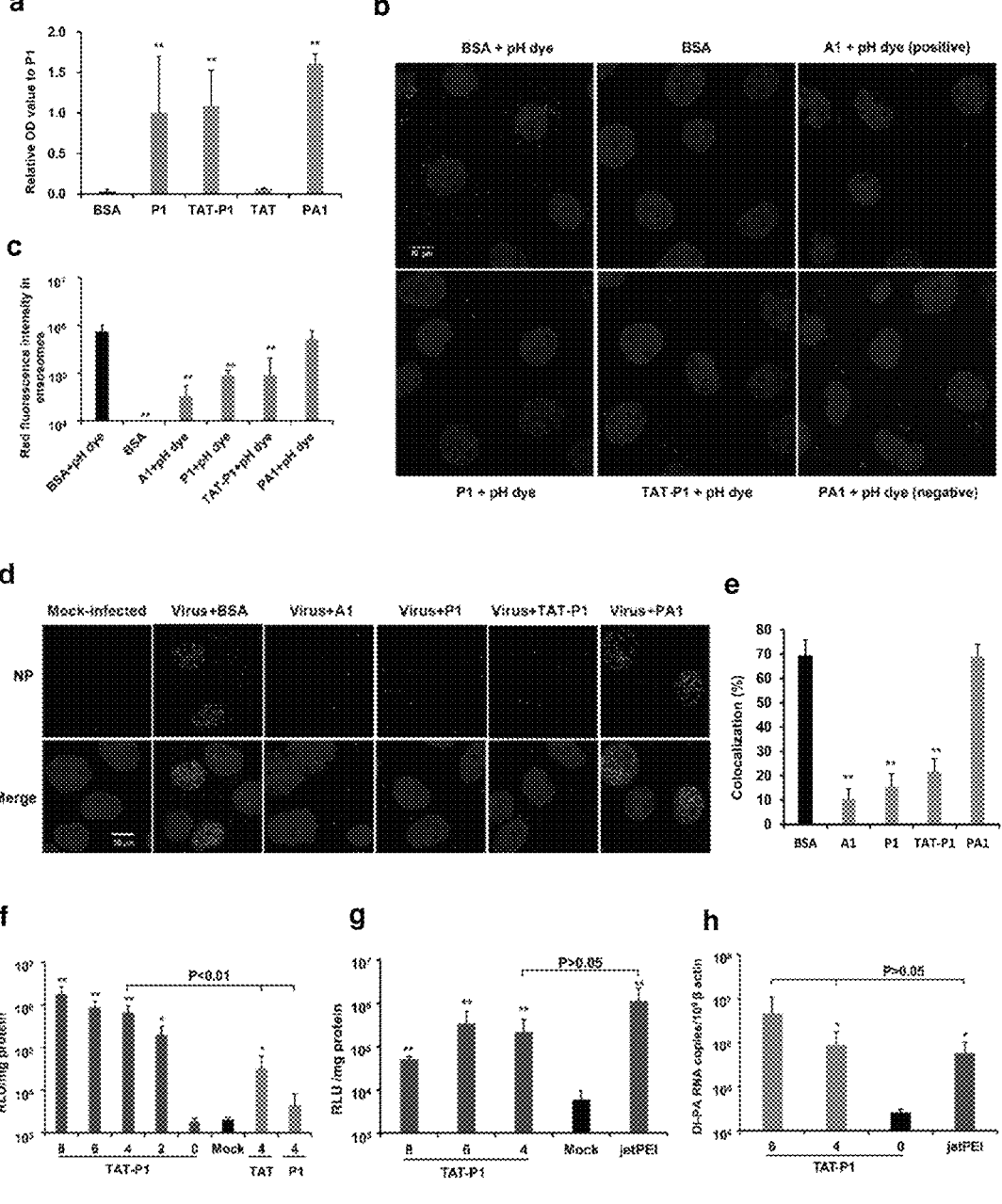

FIG. 4 The antiviral mechanism and transfection efficiency of TAT-P1. (a) P1 and TAT-P1 could bind to H1N1 glycoprotein HA1 in an ELISA assay. OD values were normalized to P1 as 1. Significant values were compared with BSA. (b) P1 and TAT-P1 could prevent endosomal acidification. Red dots (pHrodo™ dextran) indicate pH lower than pH 6.0 in endosomes. P9-aci-1 (PA1), which did not prevent endosomal acidification, was a negative peptide control for P1. Blue color indicates nuclei. Live cell images were taken by confocal microscope (original magnification 400×, scale bar=10 µm). (c) The quantification of red fluorescence of endosomal acidification in MDCK cells when cells were treated by BSA, bafilomycin A1 (A1), P1, TAT-P1 or PA1 corresponding to (b). Ten microscope fields of each sample were included for quantification. Significant values were compared to BSA+pH dye group. (d) P1 and TAT-P1 could prevent viral RNP release into nuclei. MDCK cells were infected with 1 MOI of A(H1N1) virus treated with or without drugs. Images of NP (green) and nuclei (blue) were taken at 3.5 h post infection (scale bar=10 µm). (e) Percentages of NP colocalized to nuclei. The SD was determined from multiple microscope fields including ~200 cells for each sample. (f) Transfection efficiency of peptide/ pLuc in 293T cells. Numbers indicate weight ratios of corresponding peptide:pLuc. Mock means cells treated with TAT-P1 without DNA. Data were presented as mean±SD of three independent experiments. (g) Transfection efficiency of pCMV-Luc transfected by TAT-P1 or jetPEI® transfection agent in mouse lungs. Luciferase expression in mouse lungs were normalized to 1 mg protein. Mock means mice treated with TAT-P1 or jetPEI® transfection agent without DNA. (h) Transfection efficiency of plasmid of DI-PA transfected by TAT-P1 or jetPEI® transfection agent in mouse lungs. Data were presented as mean±SD of ≥three mice in each group. * indicates P<0.05. ** indicates P<0.01 when compared with Mock in (e and f) or compared with '0' (naked DNA) in (g).

Figure 5:
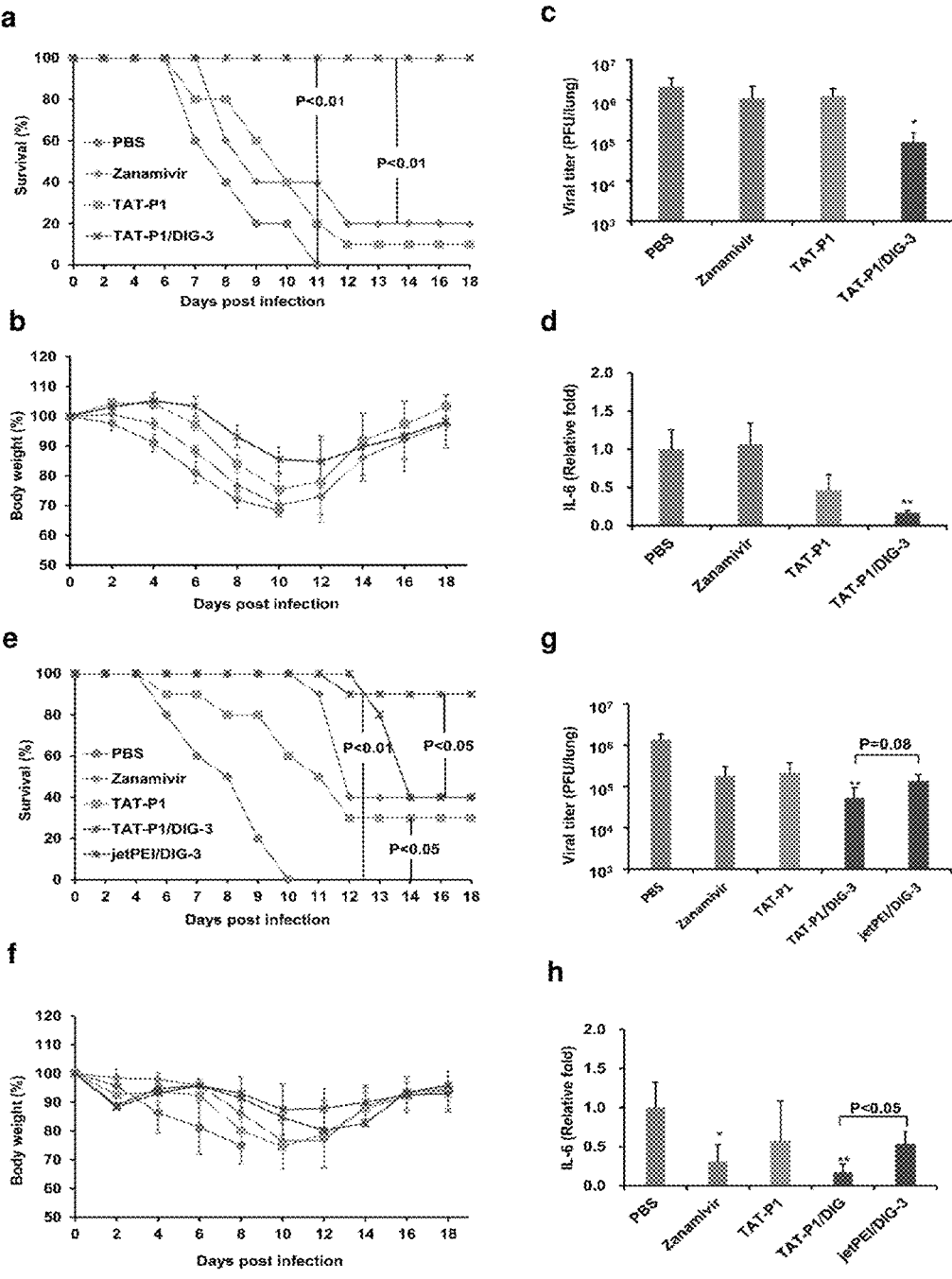

FIG. 5 TAT-P1/DIG-3 could provide prophylactic and therapeutic protection against A(H7N7) virus infection in mice. (a-d) Prophylactic efficacy of TAT-P1/DIG-3 against A(H7N7) virus. (e-h) Therapeutic efficacy of TAT-P1/DIG-3 against A(H7N7) virus. For prevention, 40 µl of PBS (n=10), zanamivir (50 µg in PBS, n=10), TAT-P1 (20 µg in distilled water, n=10), and TAT-P1/DIG (20 µg/5 µg in distilled water, n=10) were intratracheally inoculated to corresponding mice at 48 h and 24 h before viral inoculation. For therapeutic experiment, PBS (n=10), zanamivir (n=10), TAT-P1 (n=10), TAT-P1/DIG (n=10) or jetPEI/DIG (0.7 µl/5.0 µg in 5% glucose solution, n=5) were intratracheally inoculated to corresponding mice at 6 h and 24 h after viral inoculation. Viral titers and IL-6 in mouse lungs were detected at day 4 post infection with mean±SD of three mice in each group. The expression of IL-6 was normalized to PBS group. * indicates P<0.05. ** indicates P<0.01 compared with PBS group.

Figure 6:
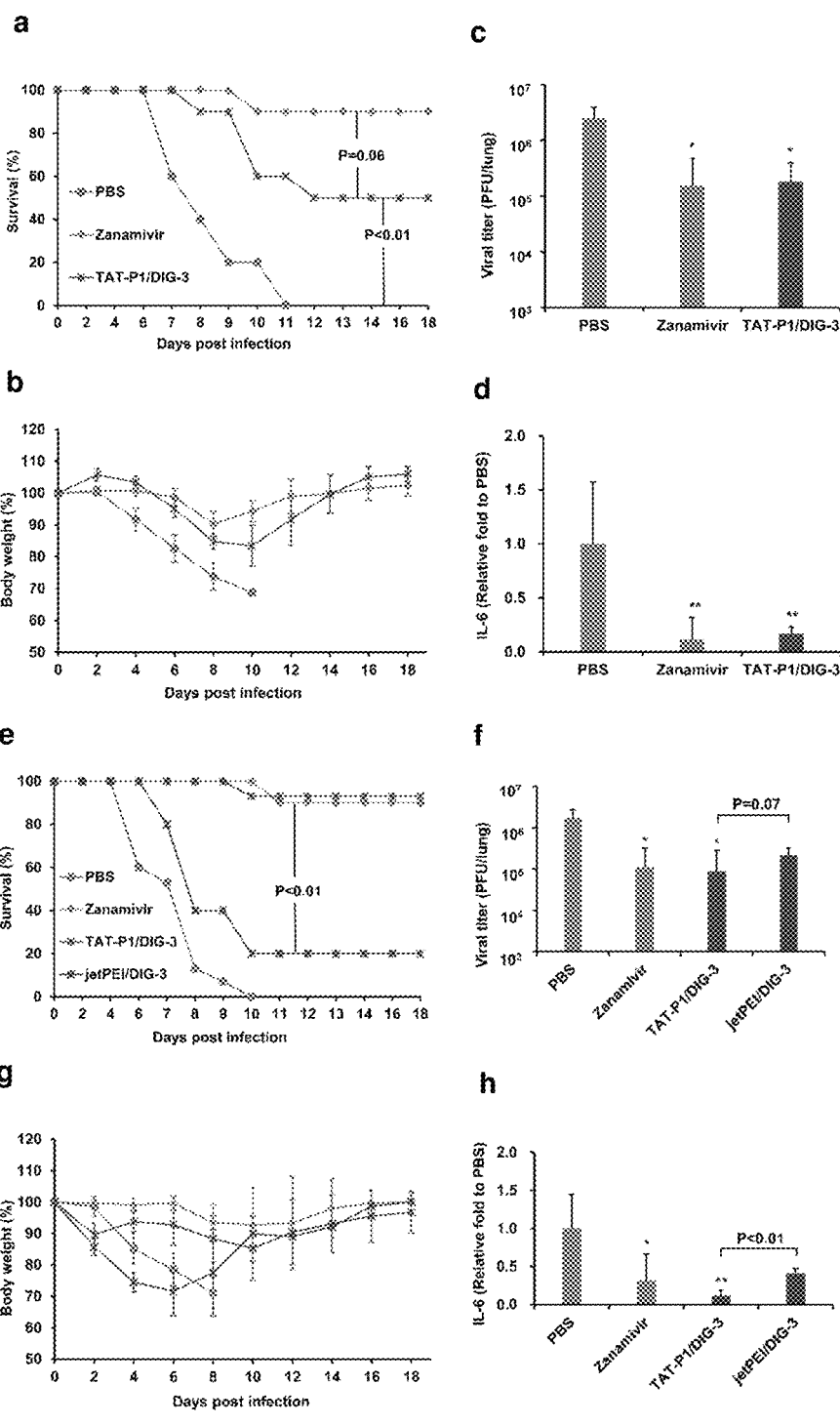

FIG. 6 TAT-P1/DIG-3 could provide prophylactic and therapeutic protection against A(H1N1)pdm09 virus infection in mice. (a-d) Prophylactic efficacy of TAT-P1/DIG-3 against A(H1N1)pdm09 virus. (e-h) Therapeutic efficacy of TAT-P1/DIG-3 against A(H1N1)pdm09 virus. For prevention, 40 µl of PBS (n=10), zanamivir (50 µg in PBS, n=10), and TAT-P1/DIG-3 (20 µg/5 µg in distilled water, n=10) were intratracheally inoculated to corresponding mice at 48 h and 24 h before viral inoculation. For therapeutic experiment, PBS (n=15), zanamivir (10), TAT-P1/DIG-3 (n=15) or jetPEI® transfection agent/DIG-3 (20 µg/5 µg in 5% glucose solution, n=5) were intratracheally inoculated to corresponding mice at 6 h and 24 h after viral inoculation. Viral titers and IL-6 in mouse lungs were detected at day 4 post infection with mean±SD of >three mice in each group. The expression of IL-6 was normalized to PBS group. * indicates P<0.05. ** indicates P<0.01 compared with PBS group.

Figure 7:
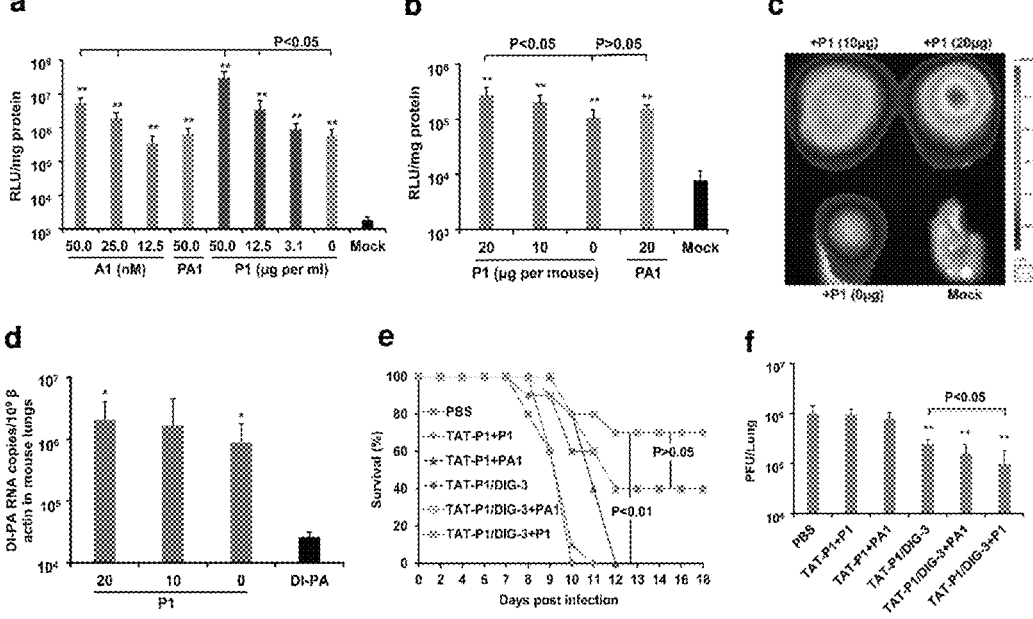

FIG. 7 The transfection efficiency and antiviral activity of TAT-P1 with DIG-3 could be increased by P1 peptide. (a) Transfection efficiency of TAT-P1/pLuc increased by additional ATPase inhibitor (bafilomycin A1) or P1 peptide. Before TAT-P1/pLuc (2.0 µg/0.5 µg) complex was added to 293T cells for transfection, the indicated concentrations of bafilomycin A1 (A1), P1 peptide or PA1 peptide were added to cell culture media. Mock indicates cells treated with A1 or TAT-P1 without DNA. Data were presented as mean±SD of three independent experiments. (b) Transfection efficiency of TAT-P1/pCMV-Luc increased by P1 in mouse lungs. (c) Representative In Vivo Imaging System image of luciferase expression increased by P1 in mouse lungs. TAT-P1/pCMV-Luc (20 µg/5 µg) with additional P1 (20 µg, 10 µg or 0 µg) or PA1 (20 µg) were inoculated to mouse lungs at 48 h and 24 h before measuring bioluminescence signal or taking bioluminescence image. Mock indicates mouse lungs inoculated with TAT-P1+P1 without DNA. (d) The RNA expression of DI-PA increased by P1 in mouse lungs.

TAT-P1/DI-PA (20 µg/5 µg) with additional P1 (20 µg, 10 µg or 0 µg) were inoculated to mouse lungs at 48 h and 24 h before detecting RNA expression. Data were presented as mean±SD of ≥three mice. * indicates P<0.05 and  indicates P<0.01 when normalized to Mock (a and b) or naked plasmid of DI-PA (d). (e-f) The prophylactic efficacy of TAT-P1/DIG-3+P1 against A(H1N1)pdm09 virus. PBS (n=10), TAT-P1+P1(n=10) or TAT-P1+PA1 (20 µg+20 µg, n=5), TAT-P1/DIG-3 (20 µg/5 µg, n=10), TAT-P1/DIG-3+PA1 (20 µg/5 µg+20 µg, n=5), or TAT-P1/DIG-3+P1 (20 µg/5 µg+20 µg, n=10) were intratracheally inoculated to corresponding mice at 48 h and 24 h before viral inoculation.  indicates P<0.01 when compared with PBS.

Figure 8:
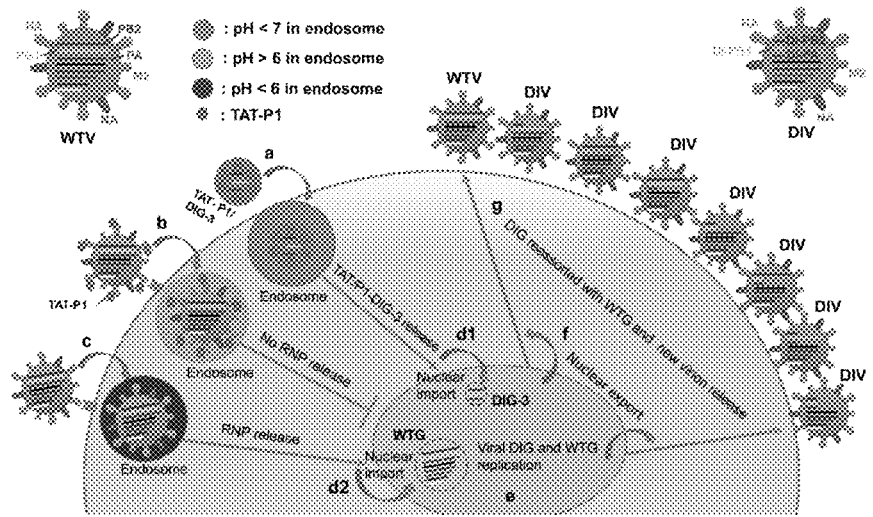

FIG. 8 Schematic model of antiviral mechanism of TAT-P1/DIG-3 in one viral life cycle. When cells are transfected with TAT-P1/DIG-3 and infected with influenza virus, (a) TAT/P1-DIG-3 are internalized into cells by endocytosis; (b) Virus can be bound with TAT-P1 and internalized into cells by endocytosis. TAT-P1 can prevent endosomal acidification to block viral RNP release into nuclei; (c) Part of virus might be internalized into cells by endocytosis and undergo endosomal acidification because of not enough or no TAT-P1 binding to virus. (d) TAT-P1/DIG-3 released from endosomes are imported into nuclei (d1) and viral RNPs released from endosomes are imported into nuclei (d2). (e) Viral DIG and wild-type genes (WTG) replicate in nuclei. (f) Newly produced DIG and WTG are exported to cytoplasm. (g) Viral DIG and WTG are reassorted in cytoplasm and move to the cell membrane to be incorporated into new virions. Seven types of DIV and one type of wild-type virus (WTV) are released from cells to start new virus life cycle. Generated DIV can keep sustained antiviral activity to competitively inhibit WTV replication in non-transfected cells.

Supplementary FIG. 1 Defective interfering gene expression in 293T and A549 cells when transfected individually. Plasmids of DI-PB2, DI-PB1, and DI-PA were transfected individually to cells. RNA was extracted from cells at 24 h post infection. Extracted RNA was digested by DNase I and then RNA expression was determined by RT-qPCR. Empty vector of phw2000 was as the negative control. Data were presented as mean±SD of three independent experiments.

Supplementary FIG. 2. Defective interfering virus did not form plaque. Viral titers of reassortant wild-type (WT: PB2-PB1-PA), DI-PB2 (DI-PB2-PB1-PA), DI-PB1 (PB2-DI-PB1-PA) or DI-PA (PB2-PB1-DI-PA) virus in the supernatants of 293T/MDCK cells. The 293T/MDCK cells were transfected with eight plasmids including eight wild-type viral genes or seven wild-type genes with one of DI-PB2, DI-PB1 or DI-PA. After 72 h post transfection, the viral titers in cell supernatants were determined by plaque assay. Data were present as mean±SD of three independent experiments.

Supplementary FIG. 3. Standard curve of HA titers to PFU titers of H7N7 virus grown in 293T and MDCK cells. Virus (1.3×107 PFU ml-1) grown in 293T cells and virus (1.0×108 PFU ml-1) grown in MDCK cells were 2-fold diluted in PBS. HA titers of each diluted virus were determined by 0.5% turkey red blood cell. Data were the average of triplicate results.

Supplementary FIG. 4. Protective efficacy of DIG-3 or single DIG on mice infected by A(H7N7) virus. (a, b) Prophylactic efficacy of jetPEI® transfection agent/DIG-3, jetPEI® transfection agent/DI-PA, jetPEI® transfection agent/DI-PB1 or jetPEI® transfection agent/PB2 against A(H7N7) virus. (c, d) Therapeutic efficacy of jetPEI® transfection agent/DIG-3 or single DIG against A(H7N7) virus. For prophylactic experiment, 40 µl of jetPEI® transfection agent/empty vector (0.7 µl/5.0 µg in 5% glucose solution), jetPEI® transfection agent/DI-PA (0.7 µl/5.0 µg in 5% glucose solution), jetPEI® transfection agent/DI-PB1, and jetPEI® transfection agent/DI-PB2 were intratracheally inoculated to corresponding mice at 48 h and 24 h before viral inoculation. For therapeutic experiment, jetPEI® transfection agent/empty vector, jetPEI® transfection agent/DI-PA, jetPEI® transfection agent/DI-PB, and jetPEI® transfection agent/DI-PB2 were intratracheally inoculated to corresponding mice at 6 h and 24 h after viral inoculation. Survivals and body weight data were generated from 10 mice in each group with mean±SD.

Supplementary FIG. 5. Peptide binding to HA1 was determined by Western blot assay. (a) Peptide sizes were shown in PAGE gel stained by Coomassie brilliant blue. (b) Binding between peptides and HA1 was confirmed by Western blot assay. One µg peptides of each was parallelly loaded to two PAGE gels. One gel was for Coomassie brilliant blue staining. The other gel was used to do Western blot assay. The peptide-transferred membrane was incubated with HA1 (2 µg ml-1) and then the binding of HA1 to peptides was determined by rabbit IgG anti-HA and goat anti-rabbit IgG-HRP.

Supplementary FIG. 6. P1 and TAT-P1 did not inhibit HA mediated membrane fusion. (a) Polykaryon formation assay. 293T cells were transfected with pH7-HA. At 24 h post transfection, cells were treated with BSA (50 µg ml-1), P1 (50 µg ml-1), FA-617 (50 µM) or TAT-P1 (10 µg ml-1) and then were further treated with pH 5.0 culture media containing the drugs. Representative Images were taken after cells were cultured for 3 hours. Polykaryons are indicated by black-white arrowheads. (b) The percentages of syncytium formation related to the control cells treated by HA-pH 5.0 were calculated from 10 microscope fields. (c) P1 and TAT-P1 could significantly inhibit viral replication in 293T cells. H7N7 virus (100 PFU) was pretreated with BSA (50 µg ml-1), P1 (50 µg/ml), TAT-P1 (10 µg ml-1) and then was inoculated to 293T cells for culture at 37° C. At 24 h post infection, cell supernatants were collected to determine the viral titers by plaque assay from three independent experiments. * indicates P<0.05 when compared with BSA.

Supplementary FIG. 7. TAT-P1 could bind DNA and form TAT-P1/DNA particles for transfection. (a) The ability of TAT-P1 binding DNA determined by gel retardation assay. (b) Particle diameter of TAT-P1/DNA was measured by DynaPro™ Plate Reader. The weight ratios of TAT-P1/DNA were indicated.

Supplementary FIG. 8. The antiviral efficacy of TAT-P1/DIG-3 against A(H7N7) virus in mice was dose dependent. TAT-P1 and DIG-3 (20 µg and 5 µg) were premixed to form TAT-P1/DIG-3 complex and incubated at room temperature for 15 min. At 48 h and 24 h before viral inoculation, TAT-P1/DIG-3 including 5.0, 2.5 and 1.3 µg of DIG-3 was inoculated to corresponding mice. Survival data were generated from five mice in each group.

Supplementary FIG. 9. A(H7N7) virus exhibited a reduced susceptibility to zanamivir when compared with A(H1N1)pdm09 virus. MDCK cells were infected with A(H7N7) and A(H1N1)pdm09 virus at an MOI of 0.005 in the presence of 0-8,000 nM of zanamivir. Supernatants were harvested at 24 h post infection and viral titers were determined by plaque assay in MDCK cells. The percentages of virus titers were normalized to the titers of virus without zanamivr treatment. Data were presented as mean±SD of three experiments.

4.1 Definitions

As used herein, the terms "nucleic acid" and "nucleotides" refer to deoxyribonucleotides, deoxyribonucleic acids, ribonucleotides, and ribonucleic acids, and polymeric forms thereof, and includes either single- or double-stranded forms. In certain embodiments, such terms include known analogues of natural nucleotides, for example, peptide nucleic acids ("PNA"s), that have similar binding properties as the reference nucleic acid. In some embodiments, such terms refer to deoxyribonucleic acids (e.g., cDNA or DNA). In other embodiments, such terms refer to ribonucleic acids (e.g., mRNA, dsRNA, shRNA, siRNA or RNA).

As used herein, the terms "prevent," "preventing" and "prevention" in the context of the administration of a therapy(ies) to a subject refer to a prophylactic effect that results from the administration of a therapy or a combination of therapies. In a specific embodiment, the terms "prevent," "preventing" and "prevention" in the context of the administration of a therapy(ies) to a subject to prevent a disease refer to one or more of the following effects resulting from the administration of a therapy or a combination of therapies: (i) the inhibition or reduction in the development or onset of a disease or a symptom thereof; (ii) the inhibition or reduction in the recurrence of a disease or a symptom associated therewith; (iii) the reduction or inhibition in a pathogen infection and/or replication; (iv) the reduction or inhibition of the spread of a virus from one cell to another cell; (ii) the reduction or inhibition of the spread of a virus from one organ or tissue to another organ or tissue; and/or (iii) the reduction or inhibition of the spread of a virus from one region of an organ or tissue to another region of the organ or tissue (e.g., the reduction in the spread of a virus from the upper to the lower respiratory tract).

As used herein, the terms "subject" and "patient" are used interchangeably to refer to an animal (e.g., cats, dogs, birds, reptiles, and mammals). In a specific embodiment, a subject is a cat. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In another embodiment, a subject is a non-human mammal. In another embodiment, a subject is a human.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to an immunogenic composition.

As used herein, in some embodiments, the term "wild-type" in the context of a virus refers to the types of viruses that are prevalent, circulating and naturally producing typical outbreaks of disease.

5. DETAILED DESCRIPTION

In one embodiment, provided herein is a vector comprising one or more viral genes wherein each of the viral gene comprises a deletion to form a detective interfering gene (DIG), said vector expresses one or more nucleic acid molecules that interfere with expression of one or more wild-type viral genes that do not comprise the deletion. In one embodiments, the deletion occurs within the gene and does not involve the terminal ends of the gene. Thus, in one embodiment, the deletion is internal deletion. In one embodiment, the deletion occurs at the terminal ends of the gene which is a terminal deletion.

In certain embodiments, the deletion is about 50-100 base pair, 100-150 base pair, 150-200 base pair, 200-250 base pair, 250-300 base pair, 300-350 base pair, 350-400 base pair, 400-450 base pair, 450-500 base pair, 500-550 base pair, 550-600 base pair, 600-650 base pair, 650-700 base pair, 700-750 base pair, 750-800 base pair, 800-850 base pair, 850-900 base pair, 900-950 base pair, 950-1000 base pair, 1000-1200 base pair, 1200-1500 base pair, 1500-1800 base pair, 1800-2100 base pair in length.

In certain embodiments, the DIG is a defective viral polymerase gene. In certain embodiments, the viral polymerase gene is PB2, PB1 or PA. In certain embodiments, the DIG comprises PB2, PB1 and PA. In certain embodiments, the DIG is DIG-3. In certain embodiments, the nucleic acid molecule interferes with expression of RNA by a wild-type virus. In certain embodiments, the nucleic acid molecule suppresses the wild-type virus from replication when transfected into cells infected with the wild-type virus. In certain embodiments, the replication of the wild-type virus is significantly reduced by the nucleic acid molecule when transfected into cells infected with the wild-type virus. In certain embodiments, the replication of the wild-type virus treated with the vector is reduced by about 10-20%, about 20-30%, about 30-40%, about 40-50%, about 50-60%, about 60-70%, about 70-80%, about 80-90%, about 90-100% as compared to a wild-type virus that is not treated with the vector.

In certain embodiments, the vector is jetPEI® transfection agent/DIG-3. In certain embodiments, the vector further comprises a nucleic acid molecule delivered by a dual-functional peptide TAT-P1. In certain embodiments, the vector is TAT-P1/DIG-3. In certain embodiments, the vector exerts antiviral activity by preventing endosomal acidification.

In one embodiment, provided herein is a composition comprising the vector disclosed herein and a pharmaceutical carrier.

In one embodiment, provided herein is a composition comprising the one or more nucleic acid molecules expressed from the disclosed vector and a TAT-P1 peptide.

In one embodiment, provided herein is a kit comprising the vector disclosed herein.

In one embodiment, provided herein is a medical device comprising the vector disclosed herein.

In one embodiment, provided herein is an inhaler comprising the vector disclosed herein.

In one embodiment, provided herein is a cell comprising the vector disclosed herein. In one embodiment, the cell is a human cell. In one embodiment, the cell is 293T or A549. In certain embodiments, the cell comprises vector TATP1/DIG3. In one embodiment, the cell is immunized against a virus. In certain embodiments, the virus is A(H7N7) or A(H1N1)pdm09 virus. In one embodiment, the vector is TAT-P1/DIG-3 and the virus is A(H1N1)pdm09 virus. In one embodiment, the vector further comprises a nucleic acid sequence that encodes a P1 peptide.

Provided herein is a method of preventing or treating a subject against avian or seasonal influenza virus, said method comprises administering to the subject an effective amount of the vector disclosed herein.

In one embodiment, the vector suppresses replication of wild-type virus comprising the wild-type viral genes by interfering with the expression of RNA. In one embodiment, the vector is administered to the subject intratracheally. In one embodiment, the vector is administered to the subject using an inhaler. In certain embodiments, about 3-5 µg, 5-10

µg, 10-15 µg, or 15-20 µg/dose of DIG-3 is administered to the subject. In certain embodiments, the vector is administered to the subject at least about 24-30 hrs, 30-36 hrs, 36-48 hrs, or 48-54 hrs prior to exposure to the virus. In certain embodiment, the vector is administered to the subject at least about 24-30 hrs, 30-36 hrs, 36-48 hrs, or 48-54 hrs after exposure to the virus.

In one embodiment, the replication of wild-type virus is significantly reduced. In certain embodiments, the replication of the wild-type virus transfected with the vector is reduced by about 10-20%, about 20-30%, about 30-40%, about 40-50%, about 50-60%, about 60-70%, about 70-80%, about 80-90%, about 90-100% as compared to wild-type virus that is not transfected with the vector.

In one embodiment, the vector is jetPEI® transfection agent/DIG-3. In one embodiment, the vector further comprises a nucleic acid molecule delivered by a dual-functional peptide TAT-P1. In one embodiment, the vector is TAT-P1/DIG-3. In one embodiment, the method further comprises administering an effective amount of P1 peptide to the subject. In one embodiment, the vector exerts antiviral activity by preventing endosomal acidification. In one embodiment, the subject is immunized against a virus. In one embodiment, the subject is animals or humans.

In certain embodiments, the virus is A(H7N7) or A(H1N1)pdm09 virus.

In one embodiment, the vector is TAT-P1/DIG-3 and the virus is A(H1N1)pdm09 virus.

In one embodiment, the subject has significantly higher survival rate than a subject that is not administered with the vector. In certain embodiments, the survival rate is about 50-100% higher than a subject that is not administered with the vector.

In one embodiment, provided herein is a fusion protein comprising HIV-1 Tat peptide (TAT) and a cationic peptide P1. In certain embodiments, the cationic peptide is P2 or P3.

In certain embodiments, the dual-functional fusion peptide is TAT-P1, TAT-P2 or TAT-P3.

Described herein are vectors, cells comprising the vectors. Also described herein are therapeutic and prophylactic compositions.

In one embodiment, provided herein are defective interfering genes (DIG-3) of influenza virus. Also provided are in vitro and in vivo antiviral effect of the defective interfering genes (DIG-3) of influenza virus. In certain embodiments, viral replication is significantly reduced in cell lines transfected with DIG-3. Mice treated with DIG-3 encoded by jetPEI® transfection agent-vector, as prophylaxis and therapeutics against A(H7N7) virus respectively, have significantly better survivals (80% and 50%) than control mice (0%). We further develop a dual-functional peptide TAT-P1, which delivers DIG-3 with high efficiency and concomitantly exerts antiviral activity by preventing endosomal acidification. TAT-P1/DIG-3 is more effective than jetPEI® transfection agent/DIG-3 in treating A(H7N7) or A(H1N1) pdm09-infected mice and shows potent prophylactic protection on A(H7N7) or A(H1N1)pdm09-infected mice. The addition of P1 peptide, which prevents endosomal acidification, can enhance the protection of TAT-P1/DIG-3 on A(H1N1)pdm09-infected mice. Dual-functional TAT-P1 with DIG-3 can effectively protect or treat mice infected by avian and seasonal influenza virus.

In certain embodiments, provided are the use of DIG as an antiviral in the treatment of influenza virus infection. In the first part, we confirmed that DIG-3 of influenza A virus PB2, PB1 and PA genes could efficiently inhibit influenza A virus replication in vitro. Transfection of DIG-3 in vivo by jetPEI could significantly protect mice from lethal A(H7N7) virus challenge. In the second part, we further improved the in vivo antiviral efficacy of DIG-3 by using a dual-functional peptide vector. This dual-functional peptide vector consists of two components, HIV-1 Tat (TAT) and P1 peptide. TAT is a peptide widely used for in vitro and in vivo transfection[18-21]. P1 peptide is a derivative of an antiviral peptide P9, which we have previously designed based on the mouse β-defensin 4 and was identified to have antiviral activity against influenza A virus H1N1, H3N2, H5N1 and H7N7[22]. Dual-functional TAT-P1 could efficiently deliver DIG-3 by transfection into mouse lung cells to inhibit viral replication and also directly inhibit viral replication by preventing endosomal acidification. We confirmed that DIG-3 delivered by TAT-P1 in mice further improved the survivals of avian A(H7N7) or human A(H1N1) virus-infected mice.

5.5 Compositions & Routes of Administration

The nucleic acid molecule described herein may be incorporated into compositions. In a specific embodiment, the compositions are pharmaceutical compositions. The pharmaceutical compositions provided herein can be in any form that allows for the composition to be administered to a subject. In a specific embodiment, the pharmaceutical compositions are suitable for veterinary and/or human administration. The compositions may be used in methods of preventing and/or treating a viral infection. The compositions may also be used in methods or preventing and/or treating a viral disease. The composition may be used in methods of delivering a certain nucleic acid molecule to a subject.

In one embodiment, a pharmaceutical composition comprises a nucleic acid molecule in an admixture with a pharmaceutically acceptable carrier. In some embodiments, a pharmaceutical composition may comprise one or more other therapies in addition to the nucleic acid molecule.

As used herein, the term "pharmaceutically acceptable" means approved by a regulatory agency of the Federal or a state government or listed in the U.S. Pharmacopeia or other generally recognized pharmacopedia for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. Liposomes or micelles can also be used as pharmaceutically acceptable carriers. These can be prepared according to methods known to those skilled in the art, for example, as described in U.S. Pat. No. 4,522,811.

In a specific embodiment, pharmaceutical compositions are formulated to be suitable for the intended route of administration to a subject. For example, the pharmaceutical composition may be formulated to be suitable for parenteral, oral, intradermal, intranasal, intratracheal, transdermal, pulmonary, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

The pharmaceutical compositions described herein can be included in a kit, container, pack, or dispenser together with instructions for administration.

6. EXAMPLES

6.1 Construction of Influenza DIG Plasmids

Influenza defective interfering PB2 (DI-PB2), DI-PB1 and DI-PA genes (Supplemental Table 5) with large internal deletion were generated from the backbone of A/WSN/1933 (H1N1) virus using fusion PCR. Each DI-PB2, DI-PB1, and DI-PA consisting of internal deletions were inserted into the phw2000 plasmid (FIG. 1a). When these plasmids of DI-PB2, DI-PB1 and DI-PA were co-transfected or individually transfected into 293T and A549 cells, 7-8 log copies per well of each DIG RNA was detected by RT-qPCR (FIG. 1b, c and Supplementary FIG. 1).

6.2 DIG Transfected Cells have Lower Viral Replication

Next, we evaluated the replication of influenza A virus in DIG transfected 293T and A549 cells. We chose A(H7N7) and A(H5N1) viruses for this in vitro assay because unlike human seasonal A(H1N1)pdm09 and A(H3N2) viruses, avian A(H7N7) and A(H5N1) viruses can replicate without trypsin in 293T or A549 cells. When 293T and A549 cells were transfected with plasmids of DI-PB2, DI-PB1 or DI-PA individually, the replication of H7N7 virus was reduced by more than 90% and 99%, respectively, compared with that of cells transfected with the empty vector (FIG. 1d). In 293T cells, the reduction of viral replication was significantly more pronounced when all three plasmids of DIG (herein referred as DIG-3, i.e. the combination of PB2 (DI-PB2), DI-PB1 and DI-PA) were co-transfected together than that when only single DIG was transfected. Although, in A549 cells, there was no significant difference between DIG-3 and single DIG, we decided to perform subsequent experiments using co-transfected DIG-3. When increasing concentration of DIG-3 was used in transfection, the antiviral efficacy against A(H7N7) virus was improved in both 293T and A549 cells in a dose-dependent manner (FIG. 1e, f). DIG-3 also showed a significant anti-A(H5N1) virus activity in both 293T and A549 cells (FIG. 1g). Collectively, these results indicated that DIG-3 could significantly inhibit both A(H7N7) and A(H5N1) virus replication in different human cell lines.

6.3 DIG-3 Outcompetes Full-Length Viral Genes and Generates DIV

In order to identify whether DIG-3 could inhibit viral replication by generating DIV, we first confirmed that DIG-3 could significantly inhibit viral replication in A549-Dual KO-RIG-I cells, which indicated that the antiviral activity of DIG-3 was not interferon dependent (FIG. 2a).

Next, we inoculated A(H7N7) virus in 293T cells that were pre-transfected with DIG-3 or the empty vector, and measured the viral RNA copies of full-length viral polymerase genes (PA, PB1 and PB2) and DI genes in cell supernatants. As shown in FIG. 2b-d, full-length PA, PB1, and PB2 RNA copies of A(H7N7) virus in the supernatants of DIG-3-transfected cells were more than 10-fold lower than those in the supernatants of empty vector-transfected cells, respectively. Importantly, RNA copies of DI-PA, DI-PB1 and DI-PB2 were 6-21 fold higher than those of full-length PA, PB1, and PB2 in the supernatants of DIG-3-transfected cells (FIG. 2b-d), indicating that significantly more DI RNAs than full-length viral RNAs were incorporated into virions to form DIV. To further confirm the generation of DIV in supernatants of DIG-3-transfected cells after wild-type A(H7N7) virus infection, we measured viral titers in the supernatants by plaque assay and HA assay and then compared the ratio of PFU and HA titer between DIG-3-transfected cells and empty vector-transfected cells (FIG. 2e). As DIV is not viable and cannot form plaques (Supplementary FIG. 2), the plaque assay measures only the wild-type plaque-forming virus without DIG, while HA assay can detect both of wild-type virus and virus containing DIG (DIV). The viral titer (PFU) in the supernatants of DIG-3-transfected 293T cells was <10% of that in the supernatants of empty vector-transfected cells. Since wild-type virus titers (PFU) correlated with HA titers in a linear fashion (Supplementary FIG. 3), it was expected that HA titer of virus in supernatants of DIG-3-transfected 293T cells was also <10% of viral titer in the supernatants of empty vector-transfected cells. However, HA titer of virus in the supernatants of DIG-3-transfected cells was about 45% of viral titer in the supernatants of empty vector-transfected cells, suggesting that virus with DIG was generated in supernatants. This is consistent to the result in FIG. 2b-d, which indicated that there were significantly higher DIG copies than full-length viral RNA copies in supernatants of DIG-3-transfected cells.

6.4 DIV Inhibits Viral Replication in Non-Transfected Cells

In FIG. 2b-e, we have shown that DIV was generated when wild-type influenza virus infected DIG-3-transfected cells. It would be important to know whether these newly generated DIV could subsequently inhibit the replication of wild-type virus in non-transfected cells. To this end, we collected the supernatant from A(H7N7)-infected 293T cells pre-transfected with DIG-3 and the supernatant from A(H7N7)-infected 293T cells pre-transfected with empty vector, and inoculated the supernatant viruses onto non-transfected MDCK cells at an MOI of 1. At 10 h post infection, MDCK cells infected with the supernatant virus from DIG-3-transfected 293T cells had a significantly lower viral titer than that of MDCK cells infected with the supernatant virus from empty vector-transfected 293T cells (FIG. 2f). The generation of DIV in MDCK cell-passaged virus was further confirmed by the higher virus titer ratio (DIG-3/empty vector) in HA assay when compared with the virus titer ratio in plaque assay (FIG. 2g) and by detecting high DI-PA RNA copies in supernatants of MDCK cells (FIG. 2h). Therefore, our data demonstrated that DIG could be packaged to generate DIV when the DIG-3-transfected cells were infected with wild-type virus, and the resultant DIV could sustain the antiviral activity by competitively inhibiting wild-type viral replication in non-transfected cells.

6.5 DIG-3 Protects Mice from Lethal Virus Challenge

To evaluate the in vivo antiviral efficacy of DIG-3, we tested prophylactic and therapeutic efficacy of DIG-3 and single DIG against influenza A virus infection in mice (FIG. 3a and Supplementary FIG. 4). The in vivo jetPEI® transfection agent, a commercially available polyethylenimine-based vector, was used to deliver DIG-3 plasmids in vivo[23,24]. The jetPEI® transfection agent and DI-PA, DI-PB1 and DI-PB2 complex (jetPEI® transfection agent/DIG-3) were delivered intratracheally. DI-PA, DI-PB1 and DI-PB2 RNAs were successfully expressed in the lungs of transfected mice at 24 h post transfection (FIG. 3b).

We first evaluated the protective efficacy of DIG-3 and single DIG on infected mice (Supplementary FIG. 4). DIG-3 showed similar prophylactic and therapeutic efficacy as DI-PB2 (Supplementary FIG. 4a-d). The survivals (80%) of mice treated by DIG-3 or DI-PB2 were slightly higher than the survivals (70%) of mice treated by DI-PB1 and DI-PA as prophylaxis, but did not reach statistical significance (Supplementary FIG. 4a). The body weight loss of mice treated by DIG-3 or DI-PB2 were also about 5-10% less than that of mice treated by DI-PA and DI-PB1 from day 10 to day 14 (Supplementary FIG. 4b). For therapeutic treatment (Supplementary FIG. 4c-d), the survival rates (40-50%) and body weight change were comparable in infected mice treated by DIG-3 or single DIG. Next, we compared the prophylactic efficacy of DIG-3 and zanamivir in mice. The jetPEI® transfection agent/DIG-3, jetPEI® transfection agent/empty vector, jetPEI® transfection agent without DIG-3, zanamivir or PBS were administered intratracheally at 48 h and 24 h before A(H7N7) infection. The survival rate of the jetPEI® transfection agent/DIG-3 group (80%) was significantly higher than that of all other control groups (≤10%) (FIG. 3c). The jetPEI® transfection agent/DIG-3 group also had significantly less body weight loss than those of zanamivir or PBS groups from day 6 to day 10 post infection (FIG. 3d). To compare the efficacy of DIG-3 and zanamivir as therapeutic treatment, jetPEI® transfection agent/DIG-3, jetPEI® transfection agent/empty vector, jetPEI® transfection agent, zanamivir or PBS were administered intratracheally at 6 h and 24 h after A(H7N7) infection. Zanamivir and jetPEI® transfection agent/DIG-3 protected 40% and 50% of mice from lethal A(H7N7) virus challenge, respectively, with no statistically significant difference. The survival of the jetPEI® transfection agent/DIG-3 group was significantly higher than that of the jetPEI® transfection agent, jetPEI® transfection agent/empty vector or PBS groups (FIG. 3e). The jetPEI® transfection agent/DIG-3 and zanamivir groups also had significantly less body weight loss than PBS group from day 6 to day 8 post infection (FIG. 3f). These results indicated that jetPEI® transfection agent/DIG-3 showed potent anti-A(H7N7) virus efficacy, which was better than zanamivir as prophylaxis and comparable to zanamivir as therapeutics against A(H7N7) virus infection in mice.

6.6 Peptide TAT-P1 Delivers Plasmid DNA In Vitro and in Mice

Although jetPEI® transfection agent/DIG-3 improved the survival rate of mice with lethal challenge by A(H7N7) virus, the survival rate was only 50% in terms of therapeutic treatment. In order to improve the effectiveness of DIG-3 as therapeutics, we investigated the use of a delivery peptide which also possesses antiviral activity. Thus, we designed three shorter derivatives of cationic peptide P9, namely P1, P2 and P3, and linked them to TAT (Supplementary Table 1). TAT-P1, TAT-P2 and TAT-P3 showed potent antiviral activity against A(H7N7) and A(H1N1)pdm09 virus, with $IC_{50}$ of <1.0 µg ml$^{-1}$ (Supplementary Table 2). TAT-P1 had the highest selective index (535) and was selected for subsequent experiments. When the antiviral activity of P1 and TAT was assessed separately (Supplementary Table 2), P1 retained the antiviral activity ($IC_{50}$=1.6 µg ml$^{-1}$), while TAT itself did not show any antiviral activity ($IC_{50}$>50.0 µg ml$^{-1}$). P1 and TAT-P1 could also bind to viral HA protein using ELISA and western blot assay (FIG. 4a and Supplementary FIG. 5). Bafilomycin A1 (A1), P1 and TAT-P1 prevented endosomal acidification (FIG. 4b, c) and blocked viral RNP release into the nuclei (FIG. 4d, e), but not the P9-aci-1 (PA1)[22] which was a negative control peptide with similar sequence as P1 (Supplementary Table 1). However, P1 and TAT-P1 did not inhibit HA-mediated membrane fusion (Supplementary FIG. 6). Therefore, P1 and TAT-P1 exerted the antiviral activity through binding to HA and preventing endosomal acidification.

Next, to evaluate the binding abilities of TAT-P1 to plasmid DNA for delivery, the ability of TAT-P1 binding DNA was detected with gel retardation assay (Supplementary FIG. 7a). It is shown that TAT-P1 could bind and form complexes with DNA when the weight ratio (peptide/DNA) was >2. The sizes of peptide/DNA complexes were determined at various peptide/DNA weight ratios (Supplementary FIG. 7b). Particles sizes between 120 nm and 180 nm were formed when complexes were prepared in water with weight ratios from 2 to 8. The in vitro transfection efficiency of TAT-P1/pLuciferase (TAT-P1/pLuc) was evaluated in 293T cells. With the increase of weight ratio (TAT-P1:pLuc) from 2 to 8, the transfection efficiency increased (FIG. 4f). The transfection efficiency of TAT-P1/pLuc was significantly higher than that of TAT/pLuc, P1/pLuc and mock-transfected cells.

We further determined whether TAT-P1 could efficiently deliver plasmid DNA into mouse lung cells. TAT-P1/pCMV-Luc or jetPEI® transfection agent/pCMV-Luc was administered intratracheally and luciferase expression was measured at 24 h post transfection. Luciferase expression in mouse lungs transfected with TAT-P1/pCMV-Luc was significantly higher than that in mouse lungs mock-transfected with TAT-P1/jetPEI® transfection agent without DNA, but was comparable to that of jetPEI® transfection agent/pCMV-Luc (FIG. 4g). When TAT-P1 and plasmid of DI-PA (TAT-P1/DI-PA) was intratracheally inoculated to mouse lungs, DI-PA RNA expression in mouse lungs was significantly higher than that in mouse lungs transfected with DI-PA without TAT-P1, but was comparable to that of jetPEI® transfection agent/DI-PA (FIG. 4h). Therefore, TAT-P1 is an effective system for in vivo transfection of plasmids. These results illustrated that TAT-P1 could directly exert antiviral activity by preventing endosomal acidification and also efficiently transfect plasmids in vivo.

6.7 TAT-P1/DIG-3 Shows Anti-A(H7N7) Virus Activity in Mice

To evaluate the prophylactic efficacy of TAT-P1/DIG-3 against viral infection in mice, different doses of TAT-P1/DIG-3 were intratracheally administered to mice at 48 h and 24 h before A(H7N7) virus infection. The survival rate of mice was increased in a dose-dependent manner and mice receiving DIG-3 at 5.0 µg per dose had 100% survival (Supplementary FIG. 8). Next, we evaluated the antiviral efficacy of mice receiving DIG-3 at 5 µg per dose and compared the result to those of zanamivir-treated and untreated controls. The survival of mice treated with TAT-P1/DIG-3 was significantly higher than that of mice treated with zanamivir, TAT-P1, or PBS (FIG. 5a). Body weight loss on day 6-10 post infection (FIG. 5b), viral titers (FIG. 5c), and the pro-inflammatory cytokine IL-6 (FIG. 5d) were significantly reduced in the TAT-P1/DIG-3-treated mice when compared with those of mice treated with zanamivir or PBS.

For therapeutic study, TAT-P1/DIG-3 and jetPEI® transfection agent/DIG-3 were intratracheally administered to mice at 6 h and 24 h post infection. TAT-P1/DIG-3-treated mice achieved a survival of 90% (FIG. 5e), and was significantly higher than that of mice treated with zanamivir (40%, P<0.05, Gehan-Breslow-Wilcoxon test) or jetPEI® transfection agent/DIG-3 (40%, P<0.05, Gehan-Breslow-Wilcoxon test). TAT-P1 could confer 30% protection to infected mice. Body weight loss on day 6-8 (FIG. 5f), viral titers (FIG. 5g), and pro-inflammatory cytokine IL-6 expression (FIG. 5h) in lung tissues were significantly reduced in mice treated with TAT-P1/DIG-3 when compared with mice treated with PBS. IL-6 was significantly lower in mice treated by TAT-P1/DIG-3 than that in mice treated by jetPEI® transfection agent/DIG-3.

6.8 TAT-P1/DIG-3 Protects Mice from A(H1N1)Pdm09 Virus Infection

To evaluate the antiviral efficacy of TAT-P1/DIG-3 against seasonal influenza virus, the prophylactic and therapeutic antiviral efficacy of TAT-P1/DIG-3 against A(H1N1)pdm09 virus were tested (FIG. 6). In prophylactic experiment (FIG. 6a-d), the survival of A(H1N1)pdm09-infected mice treated with TAT-P1/DIG-3 (50%) was lower than that of mice treated with zanamivir (90%), almost reaching statistical significance (P=0.06, Gehan-Breslow-Wilcoxon test) (FIG. 6a). TAT-P1/DIG-3 and zanamivir significantly reduced body weight loss on day 6-10 (FIG. 6b), viral titers (FIG. 6c) and IL-6 expression in mice (FIG. 6d) when compared with PBS. In therapeutic experiment (FIG. 6e-h), the survival of mice treated with TAT-P1/DIG-3 (93%) or zanamivir (90%) was significantly better than that of mice treated with PBS (0%) or jetPEI® transfection agent/DIG-3 (20%) (FIG. 6e). TAT-P1/DIG-3 significantly reduced body weight loss on day 4-8 (FIG. 6g), viral titers (FIG. 6f) and IL-6 expression (FIG. 6h) in mouse lungs when compared with PBS group. Collectively, these data of TAT-P1/DIG-3 anti-A(H7N7) and anti-A(H1N1)pdm09 virus in mice demonstrated that the dual-functional TAT-P1 could directly inhibit viral infection in mice and also efficiently deliver DIG-3 into mouse lungs to exert sustained antiviral activity for prophylactic and therapeutic treatment. Even though the prophylactic protection of TAT-P1/DIG-3 on A(H1N1)pdm09-infected mice was not as effective as zanamivir, the antiviral efficacy of TAT-P1/DIG-3 was comparable to that of zanamivir against A(H1N1)pdm09 virus in mice for therapeutic treatment and was significantly better than that of zanamivir against A(H7N7) virus for prophylactic and therapeutic treatment. The lower protection of zanamivir on A(H7N7)-infected mice than that of zanamivir on A(H1N1)pdm09-infected mice might be due to the reduced sensitivity of A(H7N7) virus to zanamivir (Supplementary FIG. 9)

6.9 P1 Improves the Prophylactic Efficacy of TAT-P1/DIG-3

The survival rate of A(H1N1)pdm09-infected mice transfected with TAT-P1/DIG-3 before viral challenge was 50%. We hypothesized that the prophylactic antiviral efficacy of TAT-P1/DIG-3 against A(H1N1)pdm09 virus could be further improved by increasing the transfection efficiency of TAT-P1/DIG-3. Previous studies showed that inhibition of endosomal acidification by ATPase inhibitor can increase the transfection efficiency of TAT[27, 28]. Using a luciferase assay, we demonstrated that the P1 peptide with inhibitory activity against endosomal acidification (FIG. 4c, d) could improve the transfection efficiency of TAT-P1/pLuc in 293T cells (FIG. 7a) and in mouse lungs (FIG. 7b). As a control, PA1 peptide, which cannot inhibit endosomal acidification (FIG. 4c, d), did not improve the transfection efficiency of TAT-P1/pLuc in 293T cells or in mouse lungs (FIG. 7 a, b). The improvement of transfection efficiency by P1 was further confirmed by images of In Vivo Imaging System (FIG. 7c) and DI-PA RNA expression in mouse lungs (FIG. 7d).

We then evaluated whether the addition of P1 peptide could improve the survival of A(H1N1)pdm09-infected mice transfected with TAT-P1/DIG-3. P1 and TAT-P1/DIG-3 were intratracheally inoculated to mice at 48 h and 24 h before A(H1N1)pdm09 virus infection. PA1 was used as a negative control. As shown in FIG. 7e, P1 combined with TAT-P1/DIG-3 (TAT-P1/DIG-3+P1) conferred an improved survival of 70% when compared with TAT-P1/DIG-3 (40%). TAT-P1/DIG-3+P1 also significantly inhibited viral replication in mouse lungs when compared with that of A(H1N1)pdm09-infected mice treated with TAT-P1/DIG-3 (FIG. 7f). PA1 peptide could not improve the survival (40%) of A(H1N1)pdm09-infected mice treated with TAT-P1/DIG-3 and did not significantly inhibit viral replication in mice when compared with that of A(H1N1)pdm09-infected mice treated with TAT-P1/DIG-3. In conclusion, these data indicated that additional P1 could further enhance the transfection efficiency of TAT-P1/DIG-3 in vivo, which conferred an improved protection on A(H1N1)pdm09-infected mice.

6.10 Discussion

In one embodiment, provided herein is the use of DIG in the treatment of avian and seasonal influenza virus infections. In one embodiment, DIG-3 significantly inhibits the replication of A(H7N7) and A(H5N1) viruses in 293T and A549 cells and protect mice from lethal A(H7N7) and A(H1N1)pdm09 virus challenge as prophylaxis or therapeutics. In one embodiment, described herein is the improved treatment efficacy of DIG-3 using a novel delivery vector TAT-P1, which also has antiviral effect via the inhibition of endosomal acidification. In one embodiment, TAT-P1/DIG-3 conferred significantly better mouse survival than that of zanamivir when used as prophylaxis or therapeutics against A(H7N7) virus in mice. In one embodiment, provided herein is the addition of P1 peptide to mouse lungs that further improve the transfection efficiency of TAT-P1/DIG-3 and the survival of mice. Also provided herein is a prophylactic and therapeutic strategy using TAT-P1/DIG-3, which interferes with the replication of a diverse subtypes of influenza virus at two steps within one life cycle of virus (FIG. 8). In one embodiment, provided herein is a novel dual-functional delivery system, TAT-P1, that directly exerts antiviral activity and transfects DIG efficiently into cells to competitively inhibit wild-type viral replication. Development of resistance against DIG is unlikely as DIG does not act on a particular viral target[16].

Concerns of DIV generating new reassortants and neutralizing antibody may exist[17]. In contrast, DIG only consists of defective genes, which will only express DI RNAs without any full-length viral RNA and will not generate new self-replicable reassortants. Furthermore, DIG will not induce the neutralizing antibody because no protein product is required for DIG induced protection[12]. In one embodiment, DI RNAs expressed by transfected plasmids in cells significantly inhibit viral replication in an interferon independent manner and be packaged to generate DIV (FIG. 2a-e), which outcompete wild-type virus[9] and showed sustained antiviral activity in non-transfected MDCK cells (FIG. 2f-h).

Peptides have been considered as promising delivery vectors in humans because of the low toxicity and the absence of toxic metabolites[40, 41]. Short peptides have been used clinically in humans as antiviral, antibacterial and anti-cancer drugs for many years[40, 42, 43]. HIV-TAT peptide, which penetrates cells in a receptor-independent manner[44], is an effective delivery peptide vector of protein and DNA through caveolae/lipid-raft-mediated endocytosis[45], micropinocytosis[27], clathrin-mediated endocytosis[46], and endocytosis-independent pathways[47]. Furthermore, the transfection efficiency of TAT could be enhanced through increasing the endosomal escape by ATPase inhibitor (chloroquine) which disrupts endosomes by preventing endosomal acidification[27]. However, chloroquine is highly toxic to cells. The effective concentrations of chloroquine ($\sim$100 $\mu$M) for inhibiting endosomal acidification are extremely toxic for cells and almost near the lethal concentration of chloroquine ($\sim$200 $\mu$M)[27, 48].

In one embodiment, provided herein is a peptide vector TAT-P1, which is expected to have less safety concerns[36]. In one embodiment, provided herein is an endosomal acidification inhibitor P1 peptide to combine with TAT. P1 possesses antiviral activity against both seasonal and avian influenza A viruses. Also, P1 can inhibit endosomal acidification with low cytotoxicity. In addition, P1 peptide could significantly enhance the transfection efficiency of plasmid DNA at a concentration (12.5 $\mu$g ml$^{-1}$) far below the CCso (>400 $\mu$g ml$^{-1}$) (FIG. 7a and Supplementary Table 2). The high transfection efficiency of TAT-P1/DIG-3 in combination with the direct antiviral activity of TAT-P1 allows the TAT-P1/DIG-3 treatment to exert the immediate antiviral activity by TAT-P1 and the sustained anti-influenza activity by DIG-3 in infected mice with low possibility to cause resistance[16].

Mice treated by TAT-P1/DIG-3 had poorer survival in the prophylactic setting (FIG. 6a and FIG. 7e) than that of therapeutic setting (FIG. 6e). One possibility is that TAT-P1 was not able to exert antiviral activity to protect mice when administered to mouse lungs at 24 h before viral inoculation in the prophylactic setting.

Challenged mice still had body weight loss despite treatment by DIG-3 encoded by jetPEI® transfection agent or TAT-P1. This is probably due to the relatively high lethal dose of influenza virus (4 LD$_{50}$) used for mouse challenge. In addition, DIG could competitively inhibit wild-type virus replication but could not completely abolish viral replication in mice. Thus, mice would be infected and lose body weight even when DIG-3 was transfected. However, since the DIG-3 could reduce viral replication, the body weight loss in the DIG-3-treated mice was much less severe than that of infected mice in the negative control groups.

In one embodiment, provided herein is a dual-functional system with both gene delivery and antiviral ability in vivo. This dual-functional TAT-P1 with DIG complex provides basis for broadly anti-influenza agents with less risk to induce antiviral resistance and establish a concept for developing transfection vectors which may have wide applications in gene antiviral strategies including the delivery of antiviral gene/siRNA to combat influenza and non-influenza viruses for treating viral respiratory diseases.

6.11 Methods

6.11.1 Cell Culture and Viruses

Madin Darby canine kidney (MDCK, CCL-34), 293T (CRL-3216) and A549 (CCL-185) cells obtained from ATCC (Manassas, VA, USA) were cultured in Dulbecco minimal essential medium (DMEM) supplemented with 10% fetal bovine serum (FBS), 100 IU ml$^{-1}$ penicillin and 100 $\mu$g ml$^{-1}$ streptomycin. A549-Dual KO-RIG-I (Invivo-Gen, USA, Cat #A549d-korigi) cells were cultured in DMEM supplemented with 10% FBS, 100 IU ml$^{-1}$ penicillin, 100 $\mu$g ml$^{-1}$ streptomycin, 10 $\mu$g ml$^{-1}$ blasticidin, 100 $\mu$g ml$^{-1}$ zeocin and 2 mM L-glutamine. The virus strains used in this study included A/Hong Kong/415742/2009[49], A/Hong Kong/415742Md/2009 (H1N1) (a highly virulent mouse-adapted strain)[50], A/Vietnam/1194/2004 (H5N1)[22] and A/Netherlands/219/2003 (H7N7)[51]. For in vitro experiments, viruses were cultured in MDCK cells. For animal experiments, viruses were cultured in eggs as described previously[52].

6.11.2 Construction of Plasmids

Plasmids containing the full-length sequence of wild-type A/WSN/1933 PA, PB1 and PB2 genes[53] were used as the template to generate defective interfering PA, PB1 and PB2 genes with internal deletion by fusion PCR[54]. Short gene segments at 5' end and 3' end of each of genes were amplified with gene specific primers (Supplementary Table 3) designed by Primer Premier 5.0. For our DI genes, we selected the 5' and 3' ends of polymerase gene segments because these regions contain the packaging signals[55, 56]. Furthermore, we chose 282-356 nt and 291-345 nt in 5' and 3' ends because previous studies showed that DI-PA, DI-PB1, and DI-PB2 genes from 291-617 nt could be isolated from infected mouse lungs[57], and the DIG with 317 nt in the 5' end and with total length of 585 nt showed highest antiviral activity[56]. The amplified short gene fragments in the 5' and 3' ends were fused by fusion PCR to generate DI-PA, DI-PB1 and DI-PB2 genes using six pairs of primers (Supplementary Table 3). The fused DI-PA, DI-PB1 and DI-PB2 genes (Supplementary Table 4) were inserted into BsmBI/BsaI sites of phw2000 vector to generate plasmids of DI-PA, DI-PB1 and DI-PB2, respectively. The DNA sequences of the constructed plasmids with DIG were verified by Sanger sequencing.

6.11.3 Antiviral Activity Assay of DIG in Cells

For in vitro antiviral experiments, plasmids of DI-PA, DI-PB1, DI-PB2 and empty vector phw2000 were transfected into 293T and A549 cells by Lipofectamine 3000 reagent according to the manufacturer's instructions (Invitrogen, Cat #1857483). After 24 h transfection, cells were washed with PBS and were inoculated with 1000 PFU of A(H7N7) or A(H5N1) virus in DMEM for infection and culture. Supernatant was collected at 40 h post infection. Viral titers were determined using plaque assay as we described previously[51].

6.11.4 Viral RNA Extraction and Reverse Transcription Quantitative PCR

Viral RNA was extracted by Viral RNA Mini Kit (QIAGEN, Cat #52906, USA) according to the manufacturer's instructions. Extracted RNA were treated with DNase I (QIAGEN, Cat #79254, USA) endonuclease according to the manufacturer's protocol and purified by RNeasy Mini Kit (QIAGEN, Cat #74106, USA) for RNA Purification to exclude plasmid DNA contamination. Real time RT-qPCR was performed as we described previously[22]. RNA was reverse transcribed to cDNA using primer Uni-12 and PrimeScript™ II $1^{st}$ Strand cDNA synthesis Kit (Takara, Cat #6210A) using GeneAmp® PCR system 9700 (Applied Biosystems, USA). The cDNA was then amplified using specific primers (Supplementary Table 4) for DI-PA, DI-PB1, DI-PB2 and wild-type H7N7 PA, PB1, PB2 using LightCycler® 480 SYBR Green I Master reaction mix (Roach, USA). For quantitation, 10-fold serial dilutions of standard plasmid equivalent to $10^1$ to $10^6$ copies per reaction were prepared to generate the calibration curve. Real-time qPCR experiments were performed using LightCycler® 96 PCR system (Roche, USA).

6.11.5 Design and Synthesis of Peptides

P1, TAT, and the fusion peptides TAT-P1, TAT-P2 and TAT-P3 were designed as shown in Supplementary Table 1 and synthesized by ChinaPeptide (Shanghai, China). The purity of all peptides was >95%. The purity and mass of each peptide were verified by HPLC and mass spectrometry.

6.11.6 Cytotoxicity Assay

Cytotoxicity of peptides was determined by the detection of 50% toxic concentration ($TC_{50}$) using a tetrazolium-based colorimetric MTT assay as we described previously[22]. Briefly, MDCK and 293T cells were seeded in 96-well cell culture plate at an initial density of $2\times10^4$ cells per well in DMEM supplemented with 10% FBS and incubated for overnight. Cell culture media were removed and then DMEM with various concentrations of peptides and 1% FBS were added to each well. After 24 h incubation at 37° C., MTT solution (5 mg ml$^{-1}$, 10 μl per well) was added to each well. After incubation at 37° C. for 4 h, 100 μl of 10% SDS in 0.01M HCl was added to each well. After further incubation at room temperature with shaking overnight, the plates were read at $OD_{570}$ using Victor™ X3 Multilabel Reader (PerkinElmer, USA). Cell culture wells without peptides were used as the experiment control and medium only served as a blank control.

6.11.7 Plaque Reduction Assay for Antiviral Peptides

Antiviral activity of peptides was measured using a plaque reduction assay as we described previously[22]. Peptides were dissolved in 30 mM phosphate buffer (PB) containing 24.6 mM $Na_2HPO_4$ and 5.6 mM $KH_2PO_4$ at a pH of 7.4[22]. Peptides or bovine serum albumin (BSA, 0.4-50.0 μg ml$^{-1}$) were premixed with A(H7N7) or A(H1N1)pdm09 viruses in phosphate buffer at room temperature. After 1 h of incubation, peptide-virus mixture was transferred to MDCK cells. At 1 h post infection, cells were washed with PBS once, and 1% low melting agar was added to cells. Cells were fixed using 4% formalin at 40 h post infection for A(H7N7) virus and 60 h post infection for A(H1N1)pdm09 virus. Crystal blue (0.1%) was added for staining, and the number of plaques was counted.

6.11.8 ELISA Assay.

Peptides (0.1 μg per well) dissolved in $H_2O$ were coated onto ELISA plates and incubated at 4° C. overnight. Then, 2% BSA was used to block plates at 4° C. overnight. For HA binding, 2 μg ml$^{-1}$ in PB buffer of HA1 (Sino Biological Inc., Cat #11055-V08H4) was incubated with peptides at 37° C. for 1 h. The binding abilities of peptides to HA1 protein were determined by incubation with rabbit anti-His-HRP (Invitrogen, Cat #R93125, 1: 2,000) at room temperature for 30 min. The reaction was developed by adding 50 μl of TMB single solution (Life Technologies, Cat #002023) for 15 min at 37° C. and stopped with 50 μl of 1 M $H_2SO_4$. Readings were obtained in an ELISA plate reader (Victor 1420 Multilabel Counter; PerkinElmer) at 450 nm.

6.11.9 Western Blot Assay

Peptide samples (1 μg) were loaded to SDS-PAGE and transferred to the polyvinylidene difluorid (PVDF) membrane. The transferred PVGF membrane was blocked by 10% skilled milk overnight and then incubated with HA1 (2 μg ml$^{-1}$) at room temperature for 1 h, followed by incubation with rabbit-IgG anti-HA (Sino Biological Inc. Cat #11055-RP02, 1:4,000) for 1 h to detect peptide-HA1 binding. Next, Goat anti-rabbit IgG-HRP (Invitrogen, Cat #656120, 1:6, 000) was used as the secondary antibody to detect the binding at room temperature for 1 h. Finally, immunoreactive bands were visualized by Luminata Classico Western HRP Substrate (Millipore, Cat #WBLUC0500).

6.11.10 Endosomal Acidification Analysis in Live Cells

Endosomal acidification was detected with a pH-sensitive dye (pHrodo Red dextran, Invitrogen, Cat #P10361) according to the manufacturer's instructions as previously described but with slight modification[22]. First, MDCK cells were treated with P1 (25.0 μg ml$^{-1}$), TAT-P1 (3.1 μg ml$^{-1}$), bafilomycin A1 (100.0 nM), P9-aci-1 (PA1, 25.0 μg ml$^{-1}$) or BSA (25.0 μg ml$^{-1}$) at 4° C. for 15 min. Second, MDCK cells were added with 100 μg ml$^{-1}$ of pH-sensitive dye and DAPI and then incubated at 4° C. for 15 min. Before taking images, cells were further incubated at 37° C. for 15 min and then cells were washed twice with PBS. Finally, PBS was added to cells and images were taken immediately with confocal microscope (Carl Zeiss LSM 700, Germany).

6.11.11 Nucleoprotein (NP) Immunofluorescence Assay

MDCK cells were seeded on cell culture slides and were infected with A(H1N1)pdm09 virus at 1 MOI pre-treated with BSA (25.0 μg ml$^{-1}$), bafilomycin A1 (50.0 nM), P1 (25.0 μg ml$^{-1}$), TAT-P1 (5.0 μg ml$^{-1}$) or PA1 (25.0 μg ml$^{-1}$). After 3.5 h post infection, cells were fixed with 4% formalin in PBS for 1 h, and permeabilized with 0.2% Triton X-100 in PBS for 5 min. Cells were washed with PBS and then blocked with 5% BSA at room temperature for 1 h. Cells were incubated with mouse IgG anti-NP (Millipore, Cat #2817019, 1:600) at room temperature for 1 h and then washed with PBS for next incubation with secondary antibody goat anti-mouse IgG Alexa-488™ NHS ester (succinimidyl ester) (Life Technologies, Cat #1752514, 1:600) at room temperature for 1 h. Finally, cells were washed with PBS and stained with DAPI. Images were taken by confocal microscope (Carl Zeiss LSM 700, Germany).

6.11.12 Polykaryon Assay

The 293T cells were seeded into 24-well plates at $2\times10^5$ cells per well. After overnight culture, the cells were transfected with phw2000-H7N7-HA plasmid (0.6 μg per well) using Lipofectamine™ 3000 transfection reagent (Invitrogen, Cat #1857483) following the manufacturer's instruction. At 24 h after transfection, the transfection medium was replaced by DMEM containing BSA (50.0 μg ml$^{-1}$), P1 (50 μg ml$^{-1}$), TAT-P1 (10 μg ml$^{-1}$) or FA-617[58] (25 μM) and cells were incubated at 37° C. for 20 min.

Polykaryon formation was induced by exposing cells to a low pH DMEM (pH 5.0) containing the corresponding concentrations of drugs at 37° C. for 10 min. The low pH DMEM medium was replaced with fresh DMEM containing 10% FBS and cells were incubated at 37° C. for 3 h. Finally, cells were fixed with 4% formalin in PBS and stained with Giemsa (Sigma). Images were taken by microscope at 200× magnification.

6.11.13 Particle Size Measurement

According to the previous study[59], peptide/DNA complexes were prepared at various weight ratios. Peptide solution and plasmid DNA solution were prepared separately in distilled water. Equal volumes of peptide and plasmid DNA solution were mixed together to give a final volume of 4 µl containing 0.5 µg of plasmid DNA. After leaving the complexes for 15 minutes at room temperature and diluting the 4 µl complexes to 50 µl in distilled water, the particle diameter of the complexes was measured by Dyna-Pro® Plate Reader (WYATT, USA).

6.11.14 Gel Retardation Assay

According to the previous study[59], peptide/DNA complexes were prepared at various ratios with 0.5 µg plasmid DNA in 4 µl distilled water. After leaving the complexes for 15 minutes at room temperature, the samples were loaded into a 1% w/v agarose gel containing ethidium bromide nucleic acid stain. Gel electrophoresis was run in TBE buffer at 100 V for 30 min and the gel was visualized under the ultraviolet (UV) illumination.

6.11.15 In Vitro Luminescence Analysis

Peptide/DNA complexes were prepared at various weight ratios with 0.5 µg plasmid DNA in 4 µl distilled water. After incubating the complexes for 15 min at room temperature, the 293T cells in 24-well plate were transfected with the complexes including 0.1 µg of each pHW2000 plasmid encoding the PA, PB1, PB2, NP and the mini-genome of pPoLI-fluc-RT (pLuc, the firefly luciferase reporter)[51]. At 24 h after transfection, luminescence was measured using Luciferase assay system (Promega, Cat #E1910) with a Victor X3 Multilabel reader (PerkinElmer, USA). The luminescence reading was normalized to 1 mg protein.

6.11.16 In Vivo Bioluminescence Analysis

Peptide with pCMV-Cypridina Luc (pCMV-Luc, ThermoFisher, Cat #RF233236) complexes were prepared at various weight ratios with 15 µg plasmid DNA in 60 µl distilled water. After leaving the complexes for 15 min at room temperature, two doses of complexes were intratracheally inoculated to mouse lungs at 48 h and 24 h before measuring the luciferase expression in lung tissues. The jetPEI® transfection agent/pCMV-Luc (2.1 µl/15.0 µg) complexes were prepared according to the manufactory protocol as a positive control (Polyplus Transfection, Cat #201-10G). Mice inoculated with peptide or jetPEI® transfection agent only were used as the negative control. For detecting bioluminescence signal, mouse lung tissues were homogenized and centrifuged at 14,500×g for 5 min. The supernatant was used to analyze the luciferase protein expression by Cypridina luciferase flash assay kit (ThermoFisher, Cat #16168). The luciferase expression level in mouse lungs was normalized to 1 mg protein. For in vivo bioluminescence imaging, mouse lungs were taken out and then substrate was added to lungs for taking image by IVIS® Spectrum In Vivo Imaging System (PerkinElmer, USA).

6.11.17 In Vivo DI RNA Expression Analysis

TAT-P1/DIG complexes were prepared with 5.0 µg plasmid DNA in 40 µl distilled water. After leaving the complexes for 15 minutes at room temperature, two doses of complexes were intratracheally inoculated to mouse lungs at 48 h and 24 h before measuring the DIG RNA expression in lung tissues. The jetPEI® transfection agent/DIG (0.7 µl/5.0 µg) complexes were prepared according to the manufacturer's protocol as a positive control. Naked DIG was inoculated to mouse lungs as base line control. Mouse lung was harvested, flash frozen and stored in liquid nitrogen. Lung tissue was homogenized under liquid nitrogen and kept frozen at all times. Once tissue was completely homogenized in powder form, 1 ml TRIzol® Reagent (ThermoFisher, Cat #15596026) was added to solubilize the tissue by gently mixing. Total RNA was firstly extracted by TRIzol® according to the manufacturer's instructions (Invitrogen, Cat #87703). Next, the total RNA was further purified by RNeasy Mini Kit (Qiagen, Cat #74106). In order to exclude the plasmid DNA contamination, all RNA samples were treated by DNase I (QIAGEN, Cat #79254) according to the manufacturer's instructions and purified by RNeasy Mini Kit (Qiagen, Cat #74106).

6.11.18 Antiviral Analysis of DIG-3 in Mice

BALB/c female mice (Laboratory Animal Unit, The University of Hong Kong), 12-16 weeks, were kept in biosafety level 3 laboratory and given access to standard pellet feed and water ad libitum. All experimental protocols followed the standard operating procedures of the approved biosafety level 3 animal facilities and were approved by the Committee on the Use of Live Animals in Teaching and Research of the University of Hong Kong[52]. The mouse adapted A(H1N1)pdm09 and A(H7N7) viruses were used for lethal challenge in mice.

To evaluate the prophylactic efficacy, mice were intratracheally inoculated with 40 µl of PBS, zanamivir (50.0 µg in PBS), jetPEI (0.7 µl in 5% glucose solution), jetPEI/plasmids (0.7 µl/5.0 µg in 5% glucose solution), TAT-P1 (20.0 µg in distilled water), TAT-P1/plasmids (20.0 µg/5 µg in distilled water) at 48 h and 24 h before viral challenge. Next, mice were intranasally inoculated with 4 $LD_{50}$ of virus. For evaluation of the therapeutic efficacy, mice were intranasally inoculated with 4 $LD_{50}$ of virus. At 6 h and 24 h post infection, mice were intratracheally inoculated with 40 µl of PBS, zanamivir (50.0 µg in PBS), jetPEI® transfection agent (0.7 µl in 5% glucose solution), jetPEI® transfection agent/plasmids (0.7 µl/5.0 µg in 5% glucose solution), TAT-P1 (20.0 µg in distilled water), or TAT-P1/plasmids (20.0 µg/5.0 µg in distilled water). Experimental mice were randomly allocated to each group. Survivals and general conditions were monitored by two investigators for 18 days or until death. Data were collected without exclusion. For viral titer and cytokine analysis, more than three mice in each group were sacrificed at day 4 after viral challenge.

6.11.19 Statistical Analysis

The statistical significances of mouse survivals were analyzed by Gehan-Breslow-Wilcoxon test using GraphPad Prism 6 (San Diego, USA). The statistical significances of other experiments were calculated by the two-tailed Student's t test. A P value of <0.05 was considered to be statistically significant.

6.11.20 Data Availability

All data that support the conclusions of the study are available from the corresponding author upon request.

SUPPLEMENTARY TABLE 1

Sequence of peptides.

| Peptides | Peptide sequence |
|---|---|
| TAT-P1 | YGRKKRRQRRRCWGPCPTAFRQIGNCGRFRVRCCRIR (SEQ ID NO: 1) |
| TAT-P2 | YGRKKRRQRRRCWRPCPRAFRKRNCGRFRIRCCRIR (SEQ ID NO: 2) |
| TAT-P3 | YGRKKRRQRRRCWRPCPSFRQLCGRFRIRCRIR (SEQ ID NO: 3) |
| P1 | CWGPCPTAFRQIGNCGRFRVRCCRIR (SEQ ID NO: 4) |
| P2 | CWRPCPRAFRKRNCGRFRIRCCRIR (SEQ ID NO: 5) |

SUPPLEMENTARY TABLE 1-continued

Sequence of peptides.

| Peptides | Peptide sequence |
|---|---|
| P3 | CWRPCPSFRQLCGRFRIRCRIR (SEQ ID NO: 6) |
| TAT | YGRKKRRQRRR (SEQ ID NO: 7) |
| P9 | NGAICWGPCPTAFRQIG NCGHFKVRCCKIR (SEQ ID NO: 8) |
| PA1 | NGAICWGPCPTAFRQIG NCGHFKVRCCKIRDED (SEQ ID NO: 9) |

Note:
TAT is from HIV-1 Tat. P1 is derived from antiviral peptide P9[1]. These peptides were designed through secondary structure analysis by PredictProtein.
1. Zhao, H. et al. A novel peptide with potent and broad-spectrum antiviral activities against multiple respiratory viruses. *Sci Rep* 6, 22008 (2016).

SUPPLEMENTARY TABLE 2

$IC_{50}$, $TC_{50}$ and selective index of peptides

| | MDCK | | | | | |
|---|---|---|---|---|---|---|
| Peptides | $IC_{50}$ (H7N7) ($\mu$g ml$^{-1}$) | $IC_{50}$ (H1N1) ($\mu$g ml$^{-1}$) | $CC_{50}$ ($\mu$g ml$^{-1}$) | Selective index (H7) | Selective index (H1) | 293T $CC_{50}$ ($\mu$g ml$^{-1}$) |
| TAT-P1 | 0.56 | 0.67 | 300 | 535 | 447 | 226 |
| TAT-P2 | 0.97 | 0.76 | 160 | 164 | 210 | 154 |
| TAT-P3 | 0.78 | 0.68 | 207 | 265 | 304 | 205 |
| P1 | 1.56 | 1.60 | >400 | | | >400 |
| TAT | >50.0 | >50.0 | >400 | | | >400 |

Note:
$IC_{50}$s of peptides against A(H7N7) and A(H1N1)pdm09 viruses were determined from three independent experiments by plaque reduction assay.
$CC_{50}$s of peptides were detected in MDCK and 239T cells through three independent experiments.

SUPPLEMENTARY TABLE 3

Oligonucleotides used for plasmid constructions

| Plasmid | Primer | Oligonucleotide sequence (5' to 3')[a] | Restriction enzyme |
|---|---|---|---|
| pDI-PB2 | PB2-F | TATTGGTCTCAGGGAGCGAAAGCAGGTC (SEQ ID NO: 10) | BsaI |
| | PB2-MR | GGTGATACCATCACTCGGTCTG (SEQ ID NO: 11) | |
| | PB2-MF | CGCCGGATCAGACCGAGTGATGGTATCACCTAACT GAAGACCCAGATGAAGGC (SEQ ID NO: 12) | |
| | PB2-R | ATATGGTCTCGTATTAGTAGAAACAAGGTCGTTT (SEQ ID NO: 13) | BsaI |
| pDI-PB1 | PB1-F | TATTCGTCTCAGGGAGCAAAAGCAGGCA (SEQ ID NO: 14) | BsmBI |
| | PB1-MR | ATCTGTTTGGGCATAACCAC (SEQ ID NO: 15) | |
| | PB1-MF | ACAATGAACCAAGTGGTTATGCCCAAACAGATCAA AAGAAATCGATCCATCTTGA (SEQ ID NO: 16) | |
| | PB1-R | ATATCGTCTCGTATTAGTAGAAACAAGGCATTT (SEQ ID NO: 17) | BsmBI |
| pDI-PA | PA-F | TATTCGTCTCAGGGAGCAAAAGCAGGTAC (SEQ ID NO: 18) | BsmBI |
| | PA-MR | TCATACAAATCTGGTAGAAACTTTG (SEQ ID NO: 19) | |
| | PA-MF | AGAAACCAAAGTTTCTACCAGATTTGTATGAGAGA GTCCCCCAAAGGAGTGGA (SEQ ID NO: 20) | |
| | PA-R | ATATCGTCTCGTATTAGTAGAAACAAGGTACTT (SEQ ID NO: 21) | BsmBI |

[a]Cutting sites for restriction enzyme are underlined.

SUPPLEMENTARY TABLE 4

Oligonucleotides used for qPCR

| Gene | Primer | Oligonucleotide sequence (5' to 3') |
|---|---|---|
| H7N7-PA | PA-F' | AACTAATCTGTATGGATTCATC (SEQ ID NO: 22) |
| | PA-R' | ATCTCGATAACGCAGTACTT (SEQ ID NO: 23) |
| H7N7-PB1 | PB1-F' | ATGGCTCTTCAGCTATTCATC (SEQ ID NO: 24) |
| | PB1-R' | ATCTGATACCAACAGTCCTGC (SEQ ID NO: 25) |
| H7N7-PB2 | PB2-F' | AAACTGGGAAACTGTGAAG (SEQ ID NO: 26) |
| | PB2-R' | ATCTGCTGGAATAGCGTC (SEQ ID NO: 27) |
| DI-PA | DI-PA-F | TATTTGCAACACTACAGGGGCTG (SEQ ID NO: 28) |
| | DI-PA-R | ATGCATACAAGCTGTTGAATACCG (SEQ ID NO: 29) |
| DI-PB1 | DI-PB1-F | CACCGAAACTGGAGCACCGCAAC (SEQ ID NO: 30) |
| | DI-PB1-R | TTTGTTCATCTTCAAGTATTCCT (SEQ ID NO: 31) |
| DI-PB2 | DI-PB2-F | GATAACGGAAATGATTCCT (SEQ ID NO: 32) |
| | DI-PB2-R | TCAGAACTGCGGACTCAAC (SEQ ID NO: 33) |
| GAPDH | Gp-F | CAA TGA CCCCTT CATTGACC (SEQ ID NO: 34) |
| | Gp-R | TTG ATT TTGGAG GGATCTCG (SEQ ID NO: 35) |

SUPPLEMENTARY TABLE 4-continued

Oligonucleotides used for qPCR

| Gene | Primer | Oligonucleotide sequence (5' to 3') |
|------|--------|-------------------------------------|
| β-actin | Act-F | TGTGATGGTGGGAATGGGTCAGAA (SEQ ID NO: 36) |
| | Act-R | TGTGGTGCCAGATCTTCTCCATGT (SEQ ID NO: 37) |

SUPPLEMENTARY TABLE 5

| Gene | Oligonucleotide sequence (5' to 3') |
|------|-------------------------------------|
| DI-PA full length (SEQ ID NO: 38) | AGCAAAAGCAGGTACTGATTCAAAATGGAAGATTTTGTGCG ACAATGCTTCAATCCGATGATTGTCGAGCTTGCGGAAAAGG CAATGAAAGAGTATGGAGAGGACCTGAAAATCGAAACAAA CAAATTTGCAGCAATATGCACTCACTTGGAAGTGTGCTTCAT GTATTCAGATTTTCACTTCATCGATGAGCAAGGCGAGTCAAT AGTCGTAGAACTTGGCGATCCAAATGCACTTTTGAAGCACA GATTTGAAATAATCGAGGGAAGAGATCGCACAATAGCCTGG ACAGTAATAAACAGTATTTGCAACACTACAGGGGCTGAGAA ACCAAAGTTTCTACCAGATTTGTATGAGAGAGTCCCCCAAA GGAGTGGAGGAAGGTTCCATTGGGAAGGTCTGCAGAACTTT ATTGGCAAAGTCGGTATTCAACAGCTTGTATGCATCTCCACA ACTGGAAGGATTTTCAGCTGAATCAAGAAAACTGCTTCTTA TCGTTCAGGCTCTTAGGGACAACCTGGAACCTGGGACCTTT GATCTTGGGGGGCTATATGAAGCAATTGAGGAGTGCCTGAT TAATGATCCCTGGGTTTTGCTTAATGCTTCTTGGTTCAACTC CTTCCTCACACATGCATTGAGATAGTTGTGGCAATGCTACTA TTTGCTATCCATACTGTCCAAAAAAGTACCTTGTTTCTACT |
| DI-PB1 full length (SEQ ID NO: 39) | AGCAAAAGCAGGCAAACCATTTGAATGGATGTCAATCCGAC TTTACTTTTCTTAAAAGTGCCAGCACAAAATGCTATAAGCAC AACTTTCCCTTATACTGGAGACCCTCCTTACAGCCATGGGAC AGGAACAGGATACACCATGGATACTGTCAACAGGACACATC AGTACTCAGAAAGGGGAAGATGGACAACAAACACCGAAAC TGGAGCACCGCAACTCAACCCGATTGATGGGCCACTGCCAG AAGACAATGAACCAAGTGGTTATGCCCAAACAGATCAAAA GAAATCGATCCATCTTGAATACAAGCCAAAGAGGAATACTT GAAGATGAACAAATGTACCAAAAGTGCTGCAACTTATTTGA AAAATTCTTCCCCAGCAGTTCATACAGAAGACCAGTCGGGA TATCCAGTATGGTGGAGGCTATGGTTTCCAGAGCCCGAATT GATGCACGAATTGATTTCGAATCTGGAAGGATAAAGAAAGA GGAGTTCACTGAGATCATGAAGATCTGTTCCACCATTGAAG AGCTCAGACGGCAAAAATAGTGAATTTAGCTTGTCCTTCAT GAAAAAATGCCTTGTTTCTACT |
| DI-PB2 full length (SEQ ID NO: 40) | AGCGAAAGCAGGTCAATTATATTCAATATGGAAAGAATAAA AGAACTAAGGAATCTAATGTCGCAGTCTCGCACTCGCGAGA TACTCACAAAAACCACCGTGGACCATATGGCCATAATCAAG AAGTACACATCAGGAAGACAGGAGAAGAACCCAGCACTTA GGATGAAATGGATGATGGCAATGAAATATCCAATTACAGCA GACAAGAGGATAACGGAAATGATTCCTGAGAGAAATGAGC AGGGACAAACTTTATGGAGTAAAATGAATGACGCCGGATCA GACCGAGTGATGGTATCACCTAACTGAAGACCCAGATGAAG GCACAGCTGGAGTTGAGTCCGCAGTTCTGAGAGGATTCCTC ATTCTGGGCAAAGAAGACAGGAGATATGGACCAGCATTAA GCATAAATGAACTGAGCAACCTTGCGAAAGGAGAGAAGGC TAATGTGCTAATTGGGCAAGGAGACGTGGTGTTGGTAATGA AACGGAAACGGAACTCTAGCATACTTACTGACAGCCAGACA GCGACCAAAAGAATTCGGATGGCCATCAATTAGTGTCGAAT AGTTTAAAAACGACCTTGTTTCTACT |

REFERENCES

1. Lambert, L. C. & Fauci, A. S. Influenza vaccines for the future. N Engl J Med 363, 2036-2044 (2010).
2. Lee, J. et al. Molecular-level analysis of the serum antibody repertoire in young adults before and after seasonal influenza vaccination. Nat Med 22, 1456-1464 (2016).

3. Cheng, V. C., To, K. K., Tse, H., Hung, I. F. & Yuen, K. Y. Two years after pandemic influenza A/2009/H1N1: what have we learned? Clin Microbiol Rev 25, 223-263 (2012).
4. Hayden, F. G. Antiviral resistance in influenza viruses—implications for management and pandemic response. N Engl J Med 354, 785-788 (2006).
5. Le, Q. M. et al. Avian flu: isolation of drug-resistant H5N1 virus. Nature 437, 1108 (2005).
6. Hu, Y. et al. Association between adverse clinical outcome in human disease caused by novel influenza A H7N9 virus and sustained viral shedding and emergence of antiviral resistance. Lancet 381, 2273-2279 (2013).
7. Centers for Disease, C. & Prevention Update: drug susceptibility of swine-origin influenza A (H1N1) viruses, April 2009. MMWR Morb Mortal Wkly Rep 58, 433-435 (2009).
8. Hung, I. F. N. et al. Hyperimmune IV immunoglobulin treatment: a multicenter double-blind randomized controlled trial for patients with severe 2009 influenza A(H1N1) infection. *Chest* 144, 464-473 (2013).

9. Fonville, J. M., Marshall, N., Tao, H., Steel, J. & Lowen, A. C. Influenza Virus Reassortment Is Enhanced by Semi-infectious Particles but Can Be Suppressed by Defective Interfering Particles. *PLoS Pathog* 11, e1005204 (2015).

10. Huang, A. S. & Baltimore, D. Defective viral particles and viral disease processes. *Nature* 226, 325-327 (1970).

11. Nayak, D. P., Tobita, K., Janda, J. M., Davis, A. R. & De, B. K. Homologous interference mediated by defective interfering influenza virus derived from a temperature-sensitive mutant of influenza virus. *J Virol* 28, 375-386 (1978).

12. Meng, B. et al. Unexpected complexity in the interference activity of a cloned influenza defective interfering RNA. *Virol J* 14, 138 (2017).

13. Dimmock, N. J., Rainsford, E. W., Scott, P. D. & Marriott, A. C. Influenza virus protecting RNA: an effective prophylactic and therapeutic antiviral. *J Virol* 82, 8570-8578 (2008).

14. Dimmock, N. J. & Marriott, A. C. In vivo antiviral activity: defective interfering virus protects better against virulent Influenza A virus than avirulent virus. *J Gen Virol* 87, 1259-1265 (2006).

15. Dimmock, N. J. et al. Cloned defective interfering influenza virus protects ferrets from pandemic 2009 influenza A virus and allows protective immunity to be established. *PLoS One* 7, e49394 (2012).

16. Dimmock, N. J. & Easton, A. J. Defective interfering influenza virus RNAs: time to reevaluate their clinical potential as broad-spectrum antivirals? *J Virol* 88, 5217-5227 (2014).

17. Dimmock, N. J. & Easton, A. J. Cloned Defective Interfering Influenza RNA and a Possible Pan-Specific Treatment of Respiratory Virus Diseases. *Viruses* 7, 3768-3788 (2015).

18. Lo, S. L. & Wang, S. An endosomolytic Tat peptide produced by incorporation of histidine and cysteine residues as a nonviral vector for DNA transfection. *Biomaterials* 29, 2408-2414 (2008).

19. Arthanari, Y., Pluen, A., Rajendran, R., Aojula, H. & Demonacos, C. Delivery of therapeutic shRNA and siRNA by Tat fusion peptide targeting BCR-ABL fusion gene in Chronic Myeloid Leukemia cells. *J Control Release* 145, 272-280 (2010).

20. Liu, Z., Li, M., Cui, D. & Fei, J. Macro-branched cell-penetrating peptide design for gene delivery. *J Control Release* 102, 699-710 (2005).

21. Lavigne, M. D., Yates, L., Coxhead, P. & Gorecki, D. C. Nuclear-targeted chimeric vector enhancing nonviral gene transfer into skeletal muscle of Fabry mice in vivo. *FASEB J* 22, 2097-2107 (2008).

22. Zhao, H. et al. A novel peptide with potent and broad-spectrum antiviral activities against multiple respiratory viruses. *Sci Rep* 6, 22008 (2016).

23. Aich, J., Mabalirajan, U., Ahmad, T., Agrawal, A. & Ghosh, B. Loss-of-function of inositol polyphosphate-4-phosphatase reversibly increases the severity of allergic airway inflammation. *Nat Commun* 3, 877 (2012).

24. Ge, Q. et al. Inhibition of influenza virus production in virus-infected mice by RNA interference. *Proc Natl Acad Sci USA* 101, 8676-8681 (2004).

25. Salomone, F. et al. A novel chimeric cell-penetrating peptide with membrane-disruptive properties for efficient endosomal escape. *J Control Release* 163, 293-303 (2012).

26. Salomone, F., Cardarelli, F., Signore, G., Boccardi, C. & Beltram, F. In Vitro Efficient Transfection by CM18-Tat (11) Hybrid Peptide: A New Tool for Gene-Delivery Applications. *Plos One* 8 (2013).

27. Wadia, J. S., Stan, R. V. & Dowdy, S. F. Transducible TAT-HA fusogenic peptide enhances escape of TAT-fusion proteins after lipid raft macropinocytosis. *Nat Med* 10, 310-315 (2004).

28. Erbacher, P., Roche, A. C., Monsigny, M. & Midoux, P. Putative role of chloroquine in gene transfer into a human hepatoma cell line by DNA/lactosylated polylysine complexes. *Exp Cell Res* 225, 186-194 (1996).

29. Easton, A. J. et al. A novel broad-spectrum treatment for respiratory virus infections: influenza-based defective interfering virus provides protection against pneumovirus infection in vivo. *Vaccine* 29, 2777-2784 (2011).

30. Ott, M. G. et al. Correction of X-linked chronic granulomatous disease by gene therapy, augmented by insertional activation of MDS1-EVI1, PRDM16 or SETBP1. *Nat Med* 12, 401-409 (2006).

31. Brenner, M. K., Gottschalk, S., Leen, A. M. & Vera, J. F. Is cancer gene therapy an empty suit? *Lancet Oncol* 14, e447-456 (2013).

32. Tebas, P. et al. Gene editing of CCR5 in autologous CD4 T cells of persons infected with HIV. *N Engl J Med* 370, 901-910 (2014).

33. Balazs, A. B., Bloom, J. D., Hong, C. M., Rao, D. S. & Baltimore, D. Broad protection against influenza infection by vectored immunoprophylaxis in mice. *Nat Biotechnol* 31, 647-652 (2013).

34. Limberis, M. P. et al. Intranasal antibody gene transfer in mice and ferrets elicits broad protection against pandemic influenza. *Sci Transl Med* 5, 187ra172 (2013).

35. Dunbar, C. E. & Larochelle, A. Gene therapy activates EVI1, destabilizes chromosomes. *Nat Med* 16, 163-165 (2010).

36. Li, S. D. & Huang, L. Gene therapy progress and prospects: non-viral gene therapy by systemic delivery. *Gene Ther* 13, 1313-1319 (2006).

37. Wong, S. P., Argyros, O., Howe, S. J. & Harbottle, R. P. Systemic gene transfer of polyethylenimine (PEI)-plasmid DNA complexes to neonatal mice. *J Control Release* 150, 298-306 (2011).

38. Hunter, A. C. Molecular hurdles in polyfectin design and mechanistic background to polycation induced cytotoxicity. *Adv Drug Deliv Rev* 58, 1523-1531 (2006).

39. Moghimi, S. M. et al. A two-stage poly(ethylenimine)-mediated cytotoxicity: implications for gene transfer/therapy. *Mol Ther* 11, 990-995 (2005).

40. Kovalainen, M. et al. Novel delivery systems for improving the clinical use of peptides. *Pharmacol Rev* 67, 541-561 (2015).

41. Li, H., Tsui, T. Y. & Ma, W. Intracellular Delivery of Molecular Cargo Using Cell-Penetrating Peptides and the Combination Strategies. *Int J Mol Sci* 16, 19518-19536 (2015).

42. Fox, J. L. Antimicrobial peptides stage a comeback. *Nat Biotechnol* 31, 379-382 (2013).

43. Vigant, F., Santos, N. C. & Lee, B. Broad-spectrum antivirals against viral fusion. *Nat Rev Microbiol* 13, 426-437 (2015).

44. Frankel, A. D. & Pabo, C. O. Cellular uptake of the tat protein from human immunodeficiency virus. *Cell* 55, 1189-1193 (1988).

45. Ferrari, A. et al. Caveolae-mediated internalization of extracellular HIV-1 tat fusion proteins visualized in real time. *Mol Ther* 8, 284-294 (2003).

46. Richard, J. P. et al. Cellular uptake of unconjugated TAT peptide involves clathrin-dependent endocytosis and heparan sulfate receptors. *J Biol Chem* 280, 15300-15306 (2005).

47. Duchardt, F., Fotin-Mleczek, M., Schwarz, H., Fischer, R. & Brock, R. A comprehensive model for the cellular uptake of cationic cell-penetrating peptides. *Traffic* 8, 848-866 (2007).

48. Molina, D. K. Postmortem hydroxychloroquine concentrations in nontoxic cases. *Am J Forensic Med Pathol* 33, 41-42 (2012).

49. To, K. K. et al. Mycophenolic acid, an immunomodulator, has potent and broad-spectrum in vitro antiviral activity against pandemic, seasonal and avian influenza viruses affecting humans. *J Gen Virol* 97, 1807-1817 (2016).

50. Zheng, B. et al. D225G mutation in hemagglutinin of pandemic influenza H1N1 (2009) virus enhances virulence in mice. *Exp Biol Med* 235, 981-988 (2010).

51. Zhao, H. et al. Novel residues in the PA protein of avian influenza H7N7 virus affect virulence in mammalian hosts. *Virology* 498, 1-8 (2016).

52. Zheng, B. J. et al. Delayed antiviral plus immunomodulator treatment still reduces mortality in mice infected by high inoculum of influenza A/H5N1 virus. *Proc Natl Acad Sci USA* 105, 8091-8096 (2008).

53. Kao, R. Y. et al. Identification of influenza A nucleoprotein as an antiviral target. *Nat Biotechnol* 28, 600-605 (2010).

54. Heckman, K. L. & Pease, L. R. Gene splicing and mutagenesis by PCR-driven overlap extension. *Nat Protoc* 2, 924-932 (2007).

55. de Wit, E., Spronken, M. I., Rimmelzwaan, G. F., Osterhaus, A. D. & Fouchier, R. A. Evidence for specific packaging of the influenza A virus genome from conditionally defective virus particles lacking a polymerase gene. *Vaccine* 24, 6647-6650 (2006).

56. Duhaut, S. D. & Dimmock, N. J. Defective segment 1 RNAs that interfere with production of infectious influenza A virus require at least 150 nucleotides of 5' sequence: evidence from a plasmid-driven system. *J Gen Virol* 83, 403-411 (2002).

57. Duhaut, S. D. & Dimmock, N. J. Heterologous protection of mice from a lethal human H1N1 influenza A virus infection by H3N8 equine defective interfering virus: comparison of defective RNA sequences isolated from the DI inoculum and mouse lung. *Virology* 248, 241-253 (1998).

58. Lai, K. K. et al. Identification of Novel Fusion Inhibitors of Influenza A Virus by Chemical Genetics. *J Virol* 90, 2690-2701 (2015).

59. Lam, J. K. et al. Effective endogenous gene silencing mediated by pH responsive peptides proceeds via multiple pathways. *J Control Release* 158, 293-303 (2012).

What is claimed:

1. A vector comprising one or more viral genes wherein each of the viral genes comprises a deletion to form a detective interfering gene (DIG), the vector expresses one or more nucleic acid molecules that interfere with expression of one or more wild-type viral genes that do not comprise the deletion, the DIG consists of one or more defective genes, that express detective interfering RNAs without any full-length viral RNA and do not generate self-replicable reassortants, wherein the vector further comprises a dual-functional peptide comprising an HIV-1 Tat Peptide (TAT) and a cationic peptide comprising SEQ ID NO: 4 (P1);

the DIG is a defective viral polymerase gene;

the viral polymerase genes are PB2, PB1 and PA;

the DIG comprises defective PB2, PB1 and PA; and the DIG comprises SEQ ID NO: 38 (DI-PA), SEQ ID NO: 39 (DI-PB1) and SEQ ID NO: 40 (DI-PB2).

2. The vector of claim 1, wherein the deletion is an internal deletion.

3. The vector of claim 1, wherein the nucleic acid molecule suppresses replication of a wild-type virus when transfected into cells, animals or humans.

4. The vector of claim 3, wherein the replication of the wild-type virus treated with the vector is reduced by about 10-20%, about 20-30%, about 30-40%, about 40-50%, about 50-60%, about 60-70%, about 70-80%, about 80-90%, or about 90-100% as compared to a wild-type virus that is not treated with the vector.

5. The vector of claim 1, wherein the vector exerts antiviral activity by preventing endosomal acidification.

6. A vector comprising one or more viral genes wherein each of the viral genes comprises a deletion to form a detective interfering gene (DIG), said vector expresses one or more nucleic acid molecules that interfere with expression of one or more wild-type viral genes that do not comprise the deletion, the DIG consists of one or more defective genes, that express detective interfering RNAs without any full-length viral RNA and do not generate self-replicable reassortants, wherein the vector further comprises a dual-functional peptide comprising an HIV-1 Tat Peptide (TAT) and a cationic peptide, comprising SEQ ID NO: 4 (P1);

the DIG is a defective viral polymerase gene;

the viral polymerase genes are PB2, PB1 and PA;

the DIG comprises defective PB2, PB1 and PA; and the DIG comprises SEQ ID NO: 38 (DI-PA), SEQ ID NO: 39 (DI-PB1) and SEQ ID NO: 40 (DI-PB2), wherein the deletion is about 50-100 base pair, 100-150 base pair, 150-200 base pair, 200-250 base pair, 250-300 base pair, 300-350 base pair, 350-400 base pair, 400-450 base pair, 450-500 base pair, 500-550 base pair, 550-600 base pair, 600-650 base pair, 650-700 base pair, 700-750 base pair, 750-800 base pair, 800-850 base pair, 850-900 base pair, 900-950 base pair, 950-1000 base pair, 1000-1200 base pair, 1200-1500 base pair, 1500-1800 base pair, or 1800-2100 base pair in length.

7. The vector of claim 6, wherein the deletion is an internal deletion.

8. The vector of claim 6, wherein the nucleic acid molecule suppresses replication of a wild-type virus when transfected into cells, animals or humans.

9. The vector of claim 8, wherein the replication of the wild-type virus treated with the vector is reduced by about 10-20%, about 20-30%, about 30-40%, about 40-50%, about 50-60%, about 60-70%, about 70-80%, about 80-90%, or about 90-100% as compared to a wild-type virus that is not treated with the vector.

10. The vector of claim 6, wherein the vector exerts antiviral activity by preventing endosomal acidification.

* * * * *